United States Patent
Teng et al.

(10) Patent No.: US 11,427,544 B2
(45) Date of Patent: Aug. 30, 2022

(54) HISTONE DEACETYLASE 6 INHIBITORS AND USE THEREOF

(71) Applicants: TAIPEI MEDICAL UNIVERSITY, Taipei (TW); NATIONAL TAIWAN UNIVERSITY, Taipei (TW)

(72) Inventors: Che-Ming Teng, Taipei (TW); Jing-Ping Liou, Taipei (TW); Shiow-Lin Pan, Taipei (TW); Chia-Ron Yang, Taipei (TW)

(73) Assignees: TAIPEI MEDICAL UNIVERSITY, Taipei (TW); NATIONAL TAIWAN UNIVERSITY, Taipei (TW)

( * ) Notice: Subject to any disclaimer, the term of this patent is extended or adjusted under 35 U.S.C. 154(b) by 0 days.

(21) Appl. No.: 16/302,021

(22) PCT Filed: May 16, 2017

(86) PCT No.: PCT/US2017/032784
§ 371 (c)(1),
(2) Date: Nov. 15, 2018

(87) PCT Pub. No.: WO2017/200966
PCT Pub. Date: Nov. 23, 2017

(65) Prior Publication Data
US 2019/0284141 A1    Sep. 19, 2019

Related U.S. Application Data

(60) Provisional application No. 62/336,863, filed on May 16, 2016.

(51) Int. Cl.
| | | |
|---|---|---|
| C07D 215/38 | (2006.01) |
| A61P 31/00 | (2006.01) |
| A61P 35/00 | (2006.01) |
| A61K 9/00 | (2006.01) |
| C07D 215/12 | (2006.01) |
| C07D 215/26 | (2006.01) |
| C07D 217/02 | (2006.01) |
| C07D 217/22 | (2006.01) |
| C07D 215/40 | (2006.01) |
| A61P 25/28 | (2006.01) |
| C07D 215/42 | (2006.01) |
| C07D 215/36 | (2006.01) |
| C07D 241/42 | (2006.01) |

(52) U.S. Cl.
CPC .......... *C07D 215/38* (2013.01); *A61K 9/0053* (2013.01); *A61P 25/28* (2018.01); *A61P 31/00* (2018.01); *A61P 35/00* (2018.01); *C07D 215/12* (2013.01); *C07D 215/26* (2013.01); *C07D 215/36* (2013.01); *C07D 215/40* (2013.01); *C07D 215/42* (2013.01); *C07D 217/02* (2013.01); *C07D 217/22* (2013.01); *C07D 241/42* (2013.01)

(58) Field of Classification Search
CPC .................................................... C07D 215/38
USPC .......................................... 546/171; 514/311
See application file for complete search history.

(56) References Cited

U.S. PATENT DOCUMENTS

| 7,495,022 B2 | 2/2009 | Kim |
| 9,249,087 B2 | 2/2016 | Kozikowski |
| 2016/0264518 A1 | 9/2016 | Bair |

FOREIGN PATENT DOCUMENTS

| CN | 1764648 A | 4/2006 |
| CN | 107531660 A | 1/2018 |
| JP | 2007001885 A | 11/2007 |
| WO | 01/38322 A1 | 5/2001 |
| WO | 03/070691 A1 | 8/2003 |
| WO | 03/087066 A1 | 10/2003 |
| WO | 2004076386 A2 | 9/2004 |
| WO | 2012106343 A2 | 8/2012 |
| WO | 2012120262 A1 | 9/2012 |
| WO | 2015157504 A1 | 10/2015 |

OTHER PUBLICATIONS

Nagaoka et al., "Synthesis and cancer, etc.," European Journal of Medicinal Chemistry 41697-708 (Year: 2006).*
Maeda et al. I, "Potent histone, etc.," Bioorganic & Medicinal Chemistry 12 4351-4360. (Year: 2004).*
Maeda et al. II, "Inhibitory effects, etc.," Bio. Pharm. Bull, 28(5) 849-853. (Year: 2005).*
Kariya et al. "Cytoprotective effect, etc.," Neuroscience Letters 392 213-215. (Year: 2006).*
Patani et al. Chem,. Rev., 96, 3147-3176. (Year: 1996).*
Golub et al, Science, vol. 286, Oct. 15, 1999, pp. 531-537.*
Glaser, "HDAC Inhibitors: Clinical Update and Mechanism-Based Potential," Biochemical Pharmacology, 2007 74(5), 659-671.*
Pearce et al., Failure modes in anticancer drug discovery and development, Cancer Drug Design and Discovery Edited by Stephen Neidle, Chapter 18, pp. 424-435 (2008).*
Takai et al., "Human Ovarian, etc.," American Cancer Society, 2004; 101(12) 2760-2770.*
Simone, Oncology:Introduction, Cecil Textbook of Medicine, ed Bennett et al. W.B.Saunders CO. 20th ed, vol. 1, 1996, pp. 1004-1010.*
Gura, Systems for identifying New Drugs are Often Faulty, Cancer Models, Science, vol. 278, No. 5340, pp. 1041-1042, Nov. 1997.*
Johnson et al., Relationships between drug activity in NCI preclinical in vitro and in vivo models and early clinical trials, British Journal of Cancer (2001) 64(10): 1424-1431.*
Ouaissi et al., "Rationale for Possible, etc.," Journal of Biomedicine and Biotechnology, 2011, Article: ID 315939, 1-8.*

(Continued)

*Primary Examiner* — David K O'Dell
(74) *Attorney, Agent, or Firm* — Duane Morris LLP

(57) ABSTRACT

Disclosed is hydroxamic acid compounds of Formula (I) set forth herein. Also disclosed are a pharmaceutical composition containing such a compound and a method of using the compound for treating a condition associated with histone deacetylase 6.

8 Claims, No Drawings

(56) References Cited

OTHER PUBLICATIONS

International Search Report and Written Opinion in International Patent Application No. PCT/US17/32784, dated Aug. 28, 2017, in 7 pages.
Extended European Search Report in European Counterpart Application No. 17799969.5, dated Oct. 7, 2019, in 8 pages.
Valente, S. et al.: "Novel cinnamyl hydroxyamides and 2-aminoanilides as histone deacetylase inhibitors: Apoptotic induction and cytodifferentiation activity", CHEMMEDCHEM, vol. 6, No. 4, 2011, pp. 698-712, XP055427149.
Li, Xiaoyang, et al. "Discovery of the first N-hydroxycinnamamide-based histone deacetylase 1/3 dual inhibitors with potent oral antitumor activity." Journal of Medicinal Chemistry 57.8 (2014): 3324-3341.
Office Action in China Counterpart Application No. 201780030151.3, dated Oct. 26, 2021 in 13 pages; English translation provided.
Zhang Wannian, Modern Drug Design, China Medical Science and Technology Publishing, (May 31, 2006), 1st edition, pp. 125 and 126.

\* cited by examiner

HISTONE DEACETYLASE 6 INHIBITORS AND USE THEREOF

CROSS-REFERENCE TO RELATED APPLICATIONS

This application is a § 371 national stage entry of International Application No. PCT/US2017/032784, filed May 16, 2017, which claims priority to U.S. Provisional Patent Application No. 62/336,863, filed May 16, 2016, the entire contents of which are incorporated herein by reference.

BACKGROUND

Histone deacetylases (HDACs) are a class of enzymes that remove an acetyl group from proteins, e.g., histones and microtubules. HDACs play important roles in regulating gene expression, cell motility, and cell functions. Many HDAC inhibitors have been developed for treating various diseases, e.g., cancer.

Currently, most HDAC inhibitors in development are pan-HDAC inhibitors, which are non-selective against different HDAC isoforms. Use of pan-HDAC inhibitors results in side effects due to their poor selectivity. In addition, dose-limited toxicity is also associated with pan-HDAC inhibitors.

Histone deacetylase 6 (HDAC6), a cytoplasmic, microtubule-associated deacetylase, has attracted great attention, as one of its substrates, i.e., heat shock protein 90, is overexpressed in many cancer cell types. A selective HDAC6 inhibitor is reported to reduce the neuronal toxicity associated with use of pan-HDAC inhibitors. See Rivieccio et al., *Proc Natl Acad Sci USA*, 2009, 106, 19599-19604.

There is a need to develop selective HDAC6 inhibitors that have high efficacy and desirable safety.

SUMMARY

The present invention relates to a new class of hydroxamic acid compounds for treating a HDAC6-associated condition. These compounds unexpectedly exhibit high potency, great selectivity, and desirable safety.

In one aspect, this invention is a compound of Formula (I) shown below:

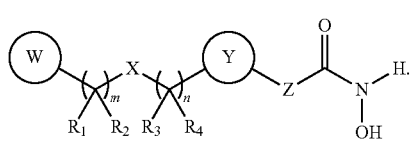

(I)

In this formula, each of $R_1$, $R_2$, $R_3$, and $R_4$, independently, is H, halo, cyano, amino, hydroxyl, —COR, —COOR, —CONR'R", $C_{1-8}$ alkyl, $C_{2-8}$ alkenyl, $C_{2-8}$ alkynyl, $C_{1-8}$ alkoxy, cycloalkyl, heterocycloalkyl, aryl, or heteroaryl; or $R_3$ and $R_4$, together with the C in $CR_3R_4$, form C=O, C=S, or C=NH, each of R, R', and R", independently, being H, $C_{1-5}$ alkyl, $C_{2-5}$ alkenyl, $C_{2-5}$ alkynyl, cycloalkyl, heterocycloalkyl, aryl, or heteroaryl; W is bicyclic aryl or bicyclic heteroaryl; X is $CR_5R_6$, O, S, or $NR_7$, each of $R_5$, $R_6$, and $R_7$, independently, being H, —COR, —COOR, —CONR'R", $C_{1-5}$ alkyl, $C_{2-5}$ alkenyl, $C_{2-5}$ alkynyl, $C_{2-5}$ alkoxy, cycloalkyl, heterocycloalkyl, aryl, or heteroaryl; Y is arylene or heteroarylene; Z is a bond, methylene, or ethylene; and each of m and n, independently, is 0 or 1.

Each of the $C_{1-5}$ alkyl, $C_{2-5}$ alkenyl, $C_{2-5}$ alkynyl, $C_{2-5}$ alkoxy, $C_{1-8}$ alkyl, $C_{2-8}$ alkenyl, $C_{2-8}$ alkynyl, $C_{1-8}$ alkoxy, cycloalkyl, heterocycloalkyl, aryl, heteroaryl, arylene, and heteroarylene is unsubstituted or substituted with halo, cyano, amino, hydroxyl, nitro, sulfhydryl, $C_{1-5}$ alkyl, $C_{2-5}$ alkoxy, cycloalkyl, heterocycloalkyl, aryl, or heteroaryl.

A subset of the compounds described above are those of formula (I), in which W is bicyclic heteroaryl, Y is arylene, m is 0, and n is 1. Examples of bicyclic heteroaryl include quinoline, isoquinoline, quinoxaline, benzopyrimidine, indole, benzoxazole, and benzothiazole. Preferably, W is quinoline, isoquinoline, or quinoxaline; more preferably, is quinolone; and; most preferably, is

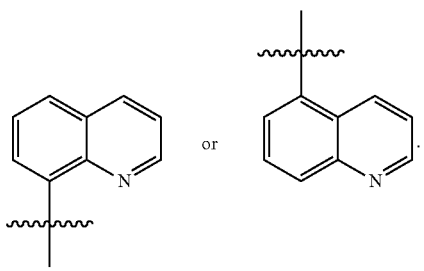 [SMILES: *c1cccc2cccnc12 ; *c1cccc2ncccc12]

An exemplary arylene is phenylene, e.g., para-phenylene and meta-phenylene.

Referring to formula (I) again, another subset of the compounds are those with X being $CH_2$, O, S, or NH.

Still another subset are those of formula (I), in which Y is para-phenylene or meta-phenylene and Z is a bond.

Further, in the above-described compounds, $R_3$ and $R_4$, together with the C in $CR_3R_4$, can form C=O.

The term "alkyl" herein refers to a straight or branched hydrocarbon group, containing 1-20 (e.g., 1-8 and 1-5) carbon atoms. Examples include methyl, ethyl, n-propyl, propyl, n-butyl, i-butyl, and t-butyl. The term "alkenyl" refers to a straight or branched hydrocarbon group, containing 2-20 (e.g., 2-8 and 2-5) carbon atoms and one or more double bonds. Examples include ethenyl and propenyl. The term "alkynyl" refers to a straight or branched hydrocarbon group, containing 2-20 (e.g., 2-8 and 2-5) carbon atoms and one or more trible bonds. Examples include ethynyl and propynyl.

The term "alkoxy" refers to an —O-alkyl group. Examples include methoxy, ethoxy, propoxy, and isopropoxy.

The term "cycloalkyl" refers to a saturated and partially unsaturated monocyclic, bicyclic, tricyclic, or tetracyclic hydrocarbon group having 3 to 12 carbons. Examples include cyclopropyl, cyclobutyl, cyclopentyl, cyclopentenyl, cyclohexyl, cyclohexenyl, cycloheptyl, and cyclooctyl.

The term "heterocycloalkyl" refers to a nonaromatic 5-8 membered monocyclic, 8-12 membered bicyclic, or 11-14 membered tricyclic ring system having one or more heteroatoms (e.g., O, N, P, and S). Examples include piperazinyl, imidazolidinyl, azepanyl, pyrrolidinyl, dihydrothiadiazolyl, dioxanyl, morpholinyl, tetrahydropuranyl, and tetrahydrofuranyl.

The term "aryl" refers to a 6-carbon monocyclic, 10-carbon bicyclic, 14-carbon tricyclic aromatic ring system, in which each ring may have 1 to 5 substituents. Examples of aryl groups include phenyl, naphthyl, and anthracenyl. The term "bicyclic aryl" refers to a 10-carbon bicyclic aromatic ring system. An exemplary bicyclic aryl is naphthyl.

The term "heteroaryl" refers to an aromatic 5-8 membered monocyclic, 8-12 membered bicyclic, or 11-14 membered tricyclic ring system having one or more heteroatoms (e.g., O, N, P, and S). Examples include triazolyl, oxazolyl, thiadiazolyl, tetrazolyl, pyrazolyl, pyridyl, furyl, imidazolyl, benzimidazolyl, pyrimidinyl, thienyl, quinolinyl, indolyl, thiazolyl, and benzothiazolyl. The term "bicyclic heteroaryl" refers to an aromatic 8-12 membered bicyclic ring system having one or more heteroatoms. Examples include benzimidazolyl and quinolinyl.

The term "arylene" refers to a bivalent radical produced by removal of two hydrogen atoms from an aryl ring. Examples include phenylene, napthylene, and anthracenylene.

The term "heteroarylene" refers to a bivalent radical produced by removal of two hydrogen atoms from a heteroaryl ring. Examples include oxazolylene, pyrazolylene, quinolinylene.

The term "halo" refers to a fluoro, chloro, bromo, or iodo radical. The term "amino" refers to a radical derived from amine, which is unsunstituted or mono-/di-substituted with alkyl, aryl, cycloalkyl, heterocycloalkyl, or heteroaryl.

Alkyl, alkenyl, alkynyl, cycloalkyl, heterocycloalkyl, alkoxy, aryl, heteroaryl, arylene, and heteroarylene mentioned herein include both substituted and unsubstituted moieties. Examples of substituents include, but are not limited to, halo, hydroxyl, amino, cyano, nitro, mercapto, alkoxycarbonyl, amido, carboxy, alkanesulfonyl, alkylcarbonyl, carbamido, carbamyl, carboxyl, thioureido, thiocyanato, sulfonamido, alkyl, alkenyl, alkynyl, alkyloxy, aryl, heteroaryl, cycloalkyl, and heterocycloalkyl, in which alkyl, alkenyl, alkynyl, alkyloxy, aryl, heteroaryl, cycloalkyl, and heterocycloalkyl may further be substituted.

Herein, the term "compound" refers to the compounds of Formula (I) described above, as well as their salts and solvates, if applicable. A salt can be formed between an anion and a positively charged group (e.g., amino) on a compound. Examples of a suitable anion include chloride, bromide, iodide, sulfate, nitrate, phosphate, citrate, methanesulfonate, trifluoroacetate, acetate, malate, tosylate, tartrate, fumarate, glutamate, glucuronate, lactate, glutarate, and maleate. A salt can also be formed between a cation and a negatively charged group. Examples of a suitable cation include sodium ion, potassium ion, magnesium ion, calcium ion, and an ammonium cation such as tetramethylammonium ion. A salt further includes those containing quaternary nitrogen atoms. A solvate refers to a complex formed between an active compound and a pharmaceutically acceptable solvent. Examples of a pharmaceutically acceptable solvent include water, ethanol, isopropanol, ethyl acetate, acetic acid, and ethanolamine.

Also within the scope of the present invention is a pharmaceutical composition for treating a HDAC6-associated condition. The HDAC6-associated condition includes cancer and neurodegenerative disorder.

The pharmaceutical composition contains a pharmaceutically acceptable carrier and one of the compounds of Formula (I) described above.

This invention also covers use of such a composition for the manufacture of a medicament for treating a HDAC6-associated condition.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. Oral solid dosage forms can be prepared by spray dried techniques; hot melt extrusion strategy, micronization, and nano milling technologies.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art. A composition having an active compound can also be administered in the form of suppositories for rectal administration.

The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an active compound. Examples of other carriers include colloidal silicon oxide, magnesium stearate, cellulose, sodium lauryl sulfate, and D&C Yellow #10.

Still within the scope of this invention is a method for treating a HDAC6-associated condition, e.g., cancer.

The method includes administering to a subject in need thereof an effective amount of a compound of Formula (I).

The above-described compounds or a pharmaceutical composition containing such a compound can be administered to a subject orally, parenterally, by inhalation spray, topically, rectally, nasally, buccally, or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques.

The term "treating" refers to application or administration of the compound to a subject with the purpose to cure, alleviate, relieve, alter, remedy, improve, or affect the disease, the symptom, or the predisposition. "An effective amount" refers to the amount of the compound which is required to confer the desired effect on the subject. Effective amounts vary, as recognized by those skilled in the art, depending on route of administration, excipient usage, and the possibility of co-usage with other therapeutic treatments such as use of other active agents.

The details of one or more embodiments of the invention are set forth in the description below. Other features, objects, and advantages of the invention will be apparent from the description and from the claims.

DETAILED DESCRIPTION

Within this invention is a compound of Formula (I):

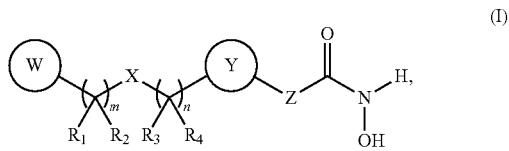

in which each of $R_1$, $R_2$, $R_3$, and $R_4$, independently, is H, halo, cyano, amino, hydroxyl, —COR, —COOR, —CONR'R", $C_{1-8}$ alkyl, $C_{2-8}$ alkenyl, $C_{2-8}$ alkynyl, $C_{1-8}$ alkoxy, cycloalkyl, heterocycloalkyl, aryl, or heteroaryl; or $R_3$ and $R_4$, together with the C in $CR_3R_4$, form C=O, C=S, or C=NH, each of R, R', and R", independently, being H, $C_{1-5}$ alkyl, $C_{2-5}$ alkenyl, $C_{2-5}$ alkynyl, cycloalkyl, heterocycloalkyl, aryl, or heteroaryl; W is bicyclic aryl or bicyclic heteroaryl; X is $CR_5R_6$, O, S, or $NR_7$, each of $R_5$, $R_6$, and $R_7$, independently, being H, —COR, —COOR, —CONR'R", $C_{1-5}$ alkyl, $C_{2-5}$ alkenyl, $C_{2-5}$ alkynyl, $C_{2-5}$ alkoxy, cycloalkyl, heterocycloalkyl, aryl, or heteroaryl; Y is arylene or heteroarylene; Z is a bond, methylene, or ethylene; and each of m and n, independently, is 0 or 1, each of the $C_{1-5}$ alkyl, $C_{2-5}$ alkenyl, $C_{2-5}$ alkynyl, $C_{2-5}$ alkoxy, $C_{1-8}$ alkyl, $C_{2-8}$ alkenyl, $C_{2-8}$ alkynyl, $C_{1-8}$ alkoxy, cycloalkyl, heterocycloalkyl, aryl, heteroaryl, arylene, and heteroarylene being unsubstituted or substituted with halo, cyano, amino, hydroxyl, nitro, sulfhydryl, $C_{1-5}$ alkyl, $C_{2-5}$ alkoxy, cycloalkyl, heterocycloalkyl, aryl, or heteroaryl, or a pharmaceutically acceptable salt thereof.

In one embodiment, the compound has W as:

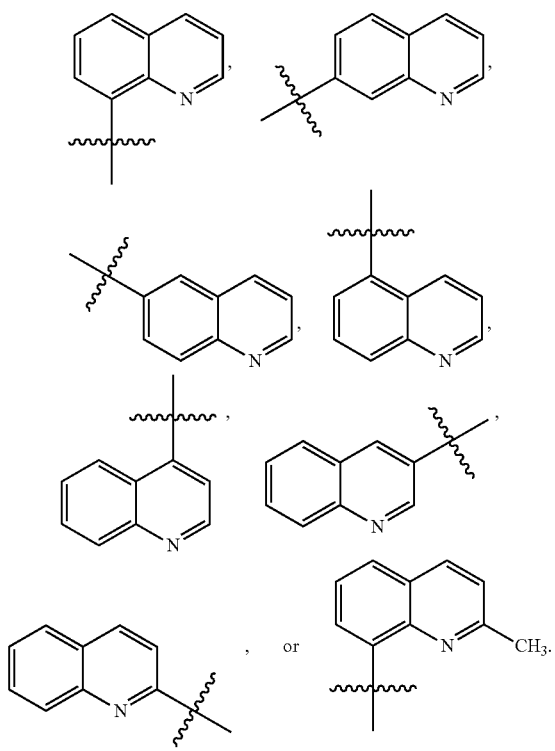

In another embodiment, the compound has W as:

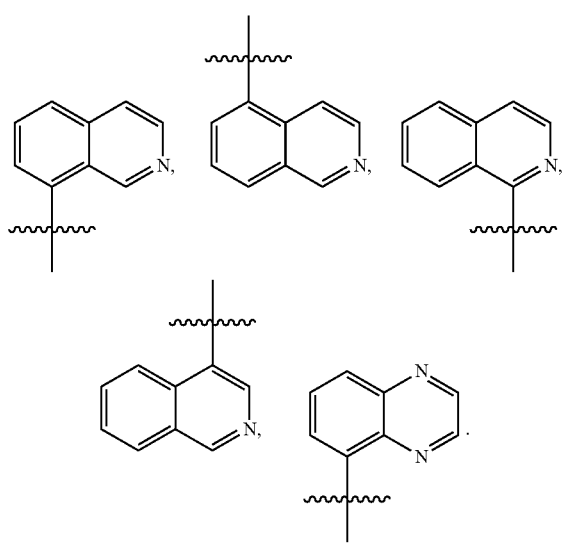

An exemplary compound of Formula (I) has each of $R_3$ and $R_4$ as H or $R_3$ and $R_4$, together with the C in $CR_3R_4$, forming C=O.

Further, this invention is a pharmaceutical composition for treating a HDAC6-associated condition, the composition containing a pharmaceutically acceptable carrier and one of the compounds of Formula (I) set forth above. The HDAC6-associated condition includes cancer and neurodegenerative disorder. Examples of the cancer include multiple myeloma, lymphoma, leukemia, colorectal cancer, and breast cancer. An exemplary neurodegenerative disorder is Alzheimer's disease.

Also covered by this invention is a method for treating a HDAC6-associated condition, the method including administering to a subject in need thereof an effective amount of a compound of Formula (I).

Methods for synthesizing the compounds of Formula (I) are well known in the art. See, for example, R. Larock, Comprehensive Organic Transformations (2nd Ed., VCH Publishers 1999); P. G. M. Wuts and T. W. Greene, Greene's Protective Groups in Organic Synthesis (4$^{th}$ Ed., John Wiley and Sons 2007); L. Fieser and M. Fieser, Fieser and Fieser's Reagents for Organic Synthesis (John Wiley and Sons 1994); L. Paquette, ed., Encyclopedia of Reagents for Organic Synthesis (2$^{nd}$ ed., John Wiley and Sons 2009); and G. J. Yu et al., J. Med. Chem. 2008, 51, 6044-6054.

The compounds of Formula (I) thus prepared can be initially screened using in vitro assays, e.g., the Fluorogenic HDAC assay described in Example 1 below, for their potency in inhibiting deacetylation of lysine residues on a substrate by recombinant HDAC proteins. They can be subsequently evaluated using in vivo assays, e.g., a tumor suppression assay, for their efficacy in suppressing tumor growth in a human multiple myeloma xenograft model. The selected compounds can be further tested to verify their efficacy in treating a HDAC6-associated condition. For example, a compound can be administered to an animal (e.g., a rat) having a HDAC6-associated condition and its therapeutic effects are then assessed. Based on the results, an appropriate dosage range and administration route can be determined.

Without further elaboration, it is believed that one skilled in the art can, based on the above description, utilize the present invention to its fullest extent. The following specific examples are, therefore, to be construed as merely illustrative, and not limitative of the remainder of the disclosure in any way whatsoever. All publications cited herein are incorporated by reference.

The following three procedures, i.e., A, B, and C, can be used to synthesize thirty-four exemplary Compounds 4, 6, 8, 10, 12, 14, 16, 18, 20, 22, 24, 26, 28, 30, 32, 34, 36, 38, 40, 42, 44, 47, 50, 52, 54, 56, 59, 61, 63, 66, 68, 71, 73, and 75, the structures of which shown below.

Procedure a for Synthesis of methyl 4-((quinolinylamino)methyl)benzoate or (E)-methyl 3-(4-((quinolinylamino)methyl)phenyl)acrylate Method A: A solution of aminoquinoline (1 equiv.) and methyl 4-formylbenzoate or (E)-methyl 3-(4-formylphenyl)acrylate (1.05 equiv.) in acetic acid (1 M) was stirred at room temperature for 30 minutes. A solution of sodium triacetoxyborohydride (2 equiv.) in acetic acid (1 M) was added dropwise into the former solution. The resulting solution was stirred at room temperature for 1 hour. Ice water was poured into the solution and the pH value of the solution was adjusted to 10 with a NaOH solution. The mixture thus formed was extracted with ethyl acetate and the top organic layer was collected. The residue concentrated from the organic layer was purified via chromatography eluted with ethyl acetate and hexane to provide a solid.

Method B: To a mixture of methyl 4-(aminomethyl)benzoate hydrochloride (1.5 equiv.) in MeOH was added NaOH (1.5 equiv.) powder at 0° C. The resulting mixture was stirred at 0° C. for 1 hour and then filtered. The filtrate was concentrated in vacuo to remove solvents. The free amine thus obtained was extracted with ethyl acetate and washed with water. Subsequently, the top organic layer was collected and dissolved in toluene (0.5 M) to form an amine solution. To a stirring mixture of bromoquinoline (1 equiv.), Pd(OAc)$_2$ (0.06 equiv.), DPEphos (0.12 equiv.), and K$_3$PO$_4$ (3 equiv.) was added the amine solution thus formed under argon protection at room temperature. The resulting mixture was heated to 100° C. for 12 hours and cooled to room temperature, and then was filtered and washed with ethyl acetate. The top organic layer was collected, concentrated, and purified via chromatography eluted with ethyl acetare and hexane to afford the desired product.

Procedure B for Synthesis of methyl 4-(quinolinyl-carbamoyl)benzoate or (E)-methyl 3-(4-((quinolinylamino)methyl)phenyl)acrylate Method A: To a solution of aminoquinoline (1.3 equiv.) and triethylamine (2 equiv.) in dichloromethane (DCM, 0.5 M) methyl 4-(chlorocarbonyl)benzoate (1 equiv.) was added in portions at 0° C. The solution thus formed was stirred at room temperature for 12 hours. The resulting solution was diluted with ethyl acetate and washed with 2 N HCl. The top organic layer was collected and concentrated in vacuo to provide the desired product.

Method B: A solution of aminoquinoline (1 equiv.), 4-dimethylaminopyridine, and monomethyl terephthalate or (E)-methyl 3-(4-formylphenyl)acrylate 1.2 equiv.) in DCM (0.1 M) was stirred at room temperature for 12 hours. Water was added to the solution and the crude reaction mixture was extracted with DCM. The collected organic layer was concentrated and purified via chromatography eluted with ethyl acetate and hexane to provide the desired product.

Procedure C for Synthesis of Benzamide or Acrylamide

To a stirring mixture of hydroxylamine hydrochloride (10 eq) in MeOH at 0° C., NaOH (10 eq) was added and the resulting mixture was then stirred for 30 minutes to form a suspension, which was subsequently filtered to provide a filtrate. The filtrate was added to the monoester obtained by Procedure B (1 eq) in MeOH (0.1 M) to form a solution. To this solution, additional NaOH (1-4 eq) was added at 0° C. and the resulting solution was maintained at room temperature for 1-24 hours. Ice water was added to the solution thus obtained and the pH was adjusted to 7 to form a precipitate. Finally, the precipitate was filtered and washed with boiling MeOH to provide benzamide or acrylamide.

Shown below are six synthetic schemes including the steps for preparing the exemplary compounds.

Scheme 1 depicts a synthetic sequence of preparing Compound 2 from the starting material 1,4-phenylbisaldehyde via an intermediate Compound 1.

Scheme 1

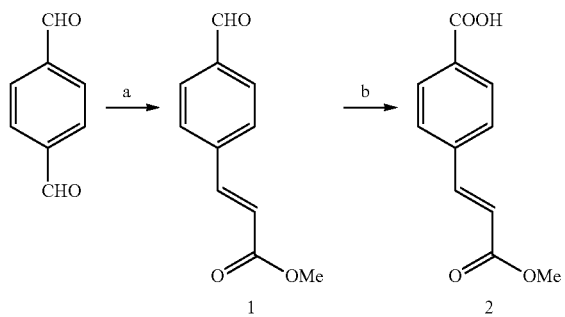

Reagents and conditions: (a) methyl 2-(triphenylphosphoranylidene)acetate, THF, room temperature; and (b) NaClO$_2$, sulfamic acid, H$_2$O-acetone, 0° C.

Scheme 2 depicts a synthetic sequence of preparing Compounds 3-6, 11-14, 19-22; and 27-30 from the starting materials aminoquinolines 2a-2d.

Scheme 2

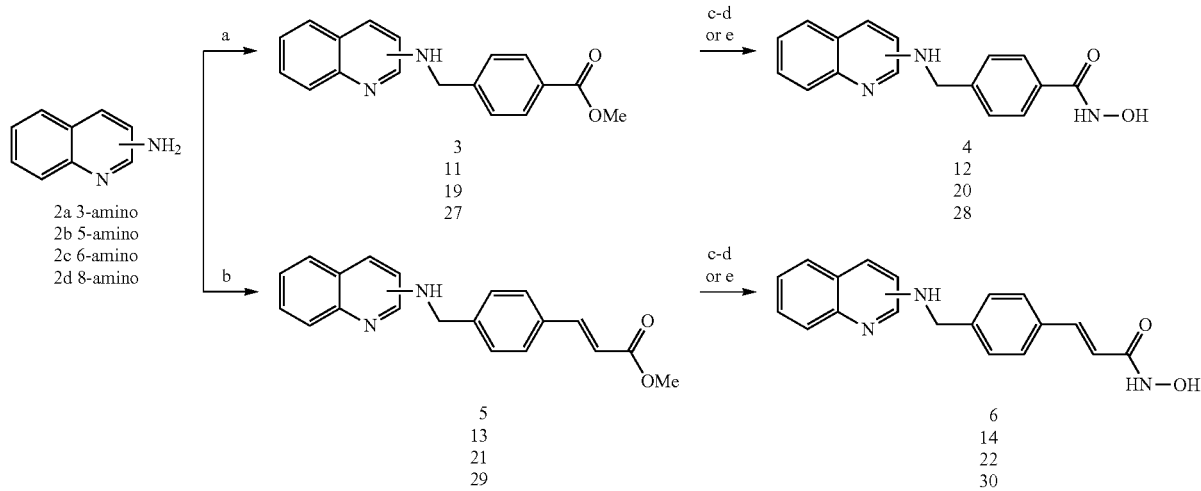

Reagents and conditions: (a) Methyl terephthalaldehydate, NaBH(OAc)$_3$, HOAc, room temperature; (b) (E)-methyl 3-(4-formylphenyl)acrylate, NaBH(OAc)$_3$, HOAc, room temperature; (c) 2N NaOH, MeOH, room temperature; (d) (i) NH$_2$OTHP, EDC-HCl, DMAP, DCM, room temperature; (ii) 1N HCl, MeOH, room temperature; and (e) NH$_2$OH, NaOH, MeOH, room temperature.

Scheme 3 depicts a synthetic sequence of preparing Compounds 39-44 from the starting materials chloro- or bromo-quinolines 3a-3c.

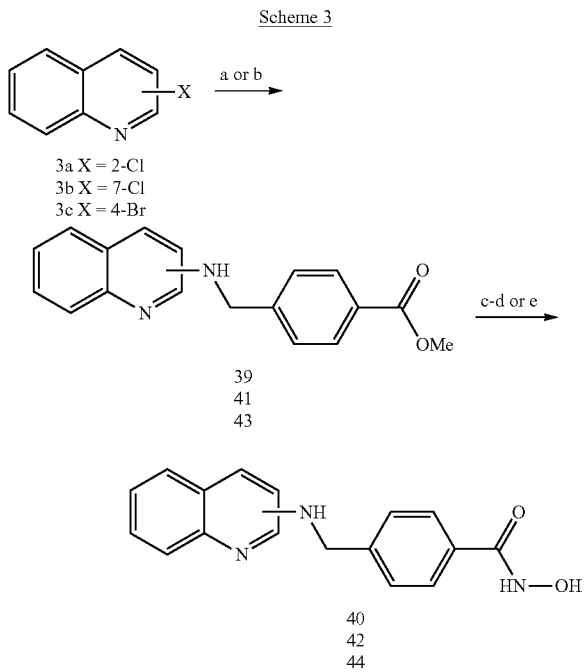

3a X = 2-Cl
3b X = 7-Cl
3c X = 4-Br 39
41
43

40
42
44

Reagents and conditions: (a) methyl 4-(aminomethyl)benzoate, Pd(OAc)$_2$, BINAP, K$_2$CO$_3$, toluene, 100° C.; (b) methyl 4-(aminomethyl)benzoate, Pd(OAc)$_2$, DPEphos, K$_3$PO$_4$, toluene, 100° C.; (c) 2N NaOH, MeOH, room temperature; (d) (i) NH$_2$OTHP, EDC-HCl, DMAP, DCM, room temperature; (ii) 1N HCl, MeOH, room temperature; and (e) NH$_2$OH, NaOH, MeOH, room temperature.

Scheme 4 depicts a synthetic sequence of preparing Compounds 7-10, 15-18, 23-26, and 31-34 from the starting materials aminoquinolines 2a-2d.

Scheme 5 depicts a synthetic sequence of preparing Compounds 53-56 and 60-63 from the starting materials chloro- or bromo-quinolines 5a-5d and 64.

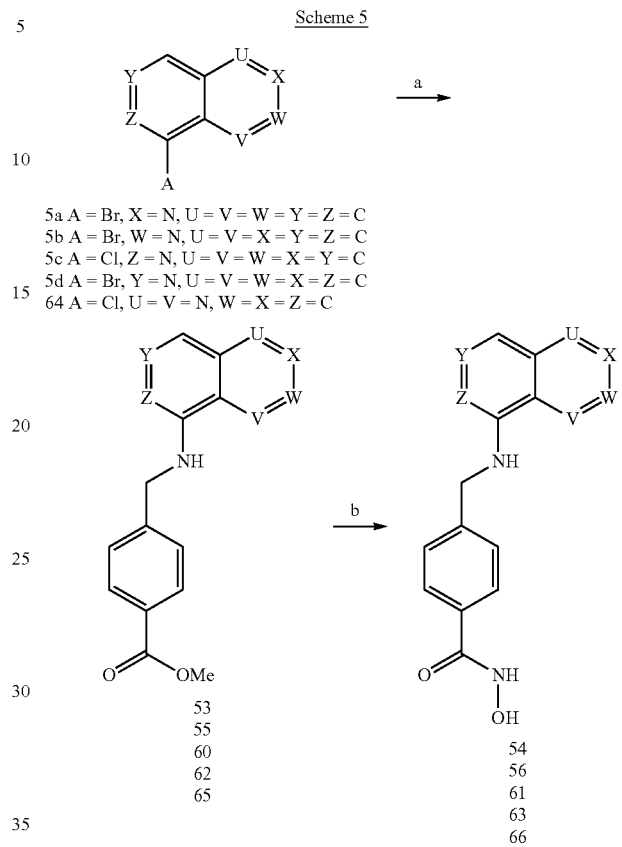

5a A = Br, X = N, U = V = W = Y = Z = C
5b A = Br, W = N, U = V = X = Y = Z = C
5c A = Cl, Z = N, U = V = W = X = Y = C
5d A = Br, Y = N, U = V = W = X = Z = C
64 A = Cl, U = V = N, W = X = Z = C 53
55
60
62
65

54
56
61
63
66

Reagents and conditions: (a) methyl 4-(aminomethyl)benzoate, Pd(OAc)$_2$, DPEphos, K$_3$PO$_4$, toluene, 100° C.; (b) 2N NaOH, MeOH, room temperature

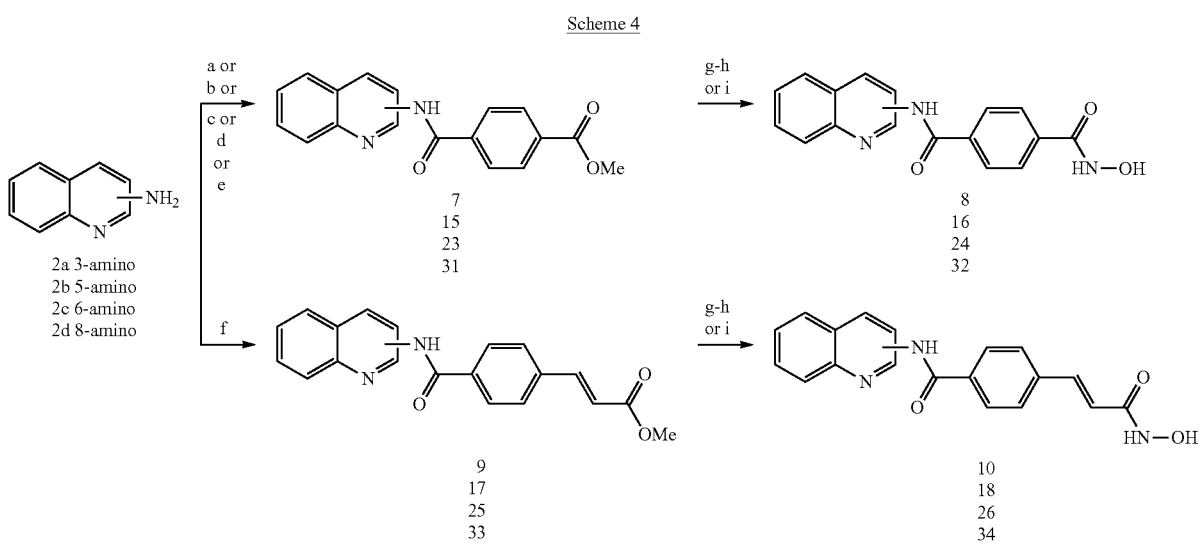

2a 3-amino
2b 5-amino
2c 6-amino
2d 8-amino 7
15
23
31

8
16
24
32

9
17
25
33

10
18
26
34

Reagents and conditions: (a) Methyl 4-(chloroformyl)benzoate, TEA, DCM, 0° C. to room temperature; (b) Monomethyl terephthalate, HBTU, TEA, DMF, room temperature to 80° C.; (c) Monomethyl terephthalate, HBTU, DIEA, DCM, room temperature to reflux; (d) Monomethyl terephthalate, EDC-HCl, DMAP (0.1 eq.), DCM, room temperature to reflux; (e) Monomethyl terephthalate, EDC-HCl, DMAP (1.0 eq.), DCM, room temperature; (f) (E)-4-(3-methoxy-3-oxoprop-1-en-1-yl)benzoic acid, EDC-HCl, DMAP (1.0 eq.), DCM, room temperature; (g) 2N NaOH, MeOH, room temperature; (h) (1) NH$_2$OTHP, EDC-HCl, DMAP, DCM, room temperature; (2) 1N HCl, MeOH, room temperature; and (i) NH$_2$OH, NaOH, MeOH, room temperature.

Scheme 6 depicts a synthetic sequence of preparing Compounds 46, 47, 50-52, 57, 59, 67-75 from the starting materials 6a-6f

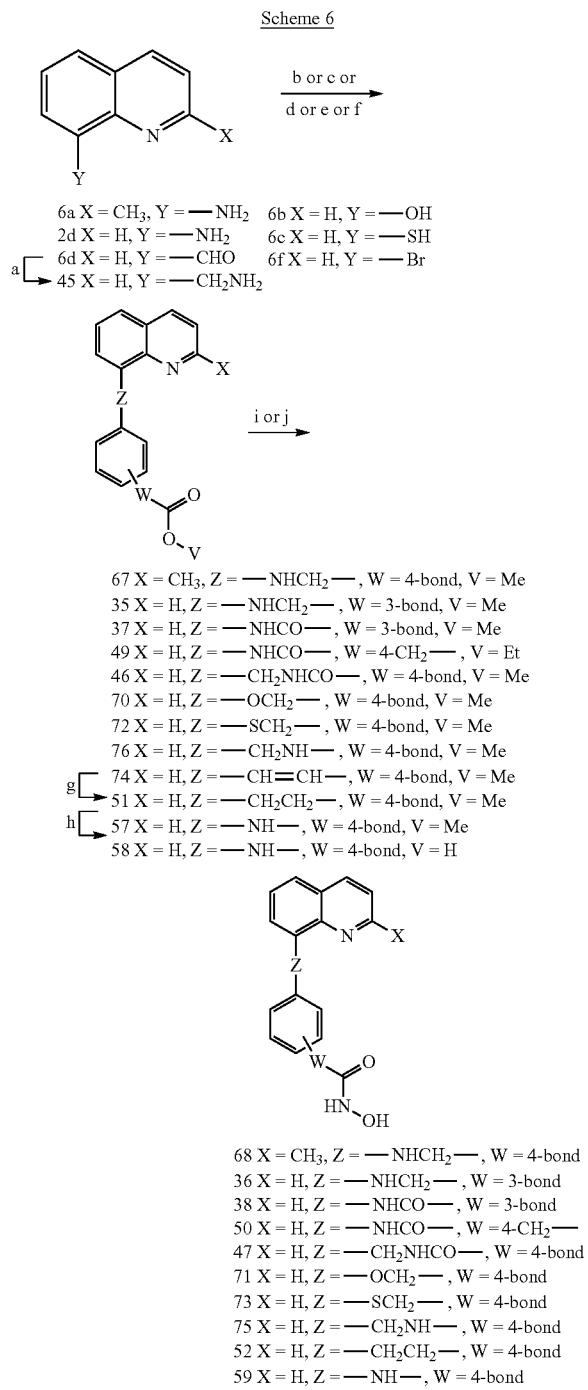

Reagents and conditions: (a) (1) t-butylcarbamate, TFA, Et₃SiH, ACN, r.t; (2) TFA, r.t; (b) Methyl terephthalaldehydate or methyl 3-formylbenzoate or methyl 4-(aminomethyl)benzoate, NaBH(OAc)₃, AcOH, r.t; (c) 3-(methoxycarbonyl)benzoic acid or, EDC-HCl, DMAP, DCM, r.t; (d) Ethyl 4-(bromomethyl)benzoate, K₂CO₃, acetone, reflux; (e) Triphenyl-(4-methoxycarbonylbenzyl)phosphonium chloride, t-BuOK, DCM, 0° C. to r.t; (f) Methyl 4-(aminomethyl)benzoate, Pd(OAc)₂, DPEphos, K₃PO₄, toluene, 100° C.; (g) Pd/C, H₂, MeOH, r.t; (h) 1N NaOH, MeOH, r.t; (i) NH₂OH, MeOH, r.t; (j) (1) NH₂-OTHP, EDC-HCl, DMAP, DCM, r.t; (2) 1N HCl, MeOH, r.t.

The methods for preparing the exemplary compounds, as well as the analytical data for the compounds thus prepared, are set forth in Examples 1-35 below.

The procedures for testing these compounds are described in Examples 36-43 also below. In Example 36, exemplary compounds are tested against HDAC1, 3, 4, 5, 6, 7, 8, 9 and Sirt1. Of note, there are eighteen human HDACs. Eleven of them, designated as HDAC1-11, are zinc-dependent. Seven of them, designated as Sirt1-7, are NAD+-dependent.

Example 1

(E)-methyl 3-(4-formylphenyl)acrylate

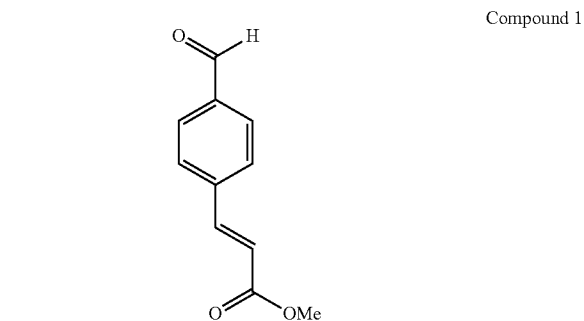 [SMILES: COC(=O)/C=C/c1ccc(C=O)cc1]

To a solution of terephthalaldehyde (5 g, 36.54 mmol) in tetrahydrofuran (THF) methyl (triphenylphosphoranylidene)acetate (13.09 g, 38.37 mmol) was added at room temperature. The solution was stirred at room temperature for 4 hours. The resulting solution was washed with water three times and the organic layer was collected. The residue was purified via chromatography eluted with ethyl acetate and hexane to provide a solid (6.17 g, 89%). $^1$H NMR (300 MHz, DMSO-$d_6$): δ 3.74 (s, 3H, OCH₃), 6.81 (d, 1H, J=16.2 Hz, CH=CH), 7.73 (d, 1H, J=16.2 Hz, CH=CH), 7.90-7.97 (m, 4H, ArH), 10.02 (brs, 1H, CHO).

(E)-4-(3-methoxy-3-oxoprop-1-en-1-yl)benzoic acid

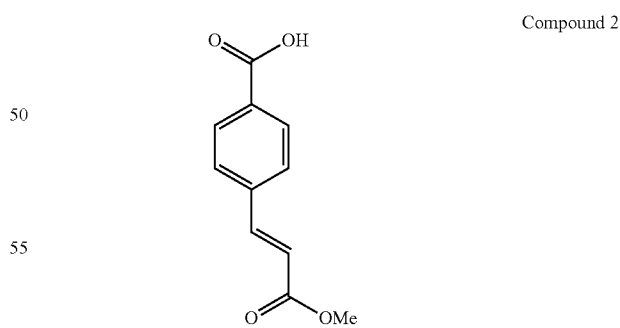

To a solution of (E)-methyl 3-(4-formylphenyl)acrylate (6 g, 31.55 mmol) in acetone (160 mL) a solution of sulfamic acid (4.64 g, 2.88 mmol) in water (80 mL) was added. The resulting solution was cooled to 0° C. and then sodium chlorite (0.26 g, 2.31 mmol) was added slowly. After 30 minutes, the solution was evaporated to give the solid. The crude solid was washed with water to provide the product (6.1 g, 93%). $^1$H NMR (300 MHz, DMSO-$d_6$): δ 3.73 (s, 3H, OCH$_3$), 6.75 (d, 1H, J=16.2 Hz, CH=CH), 7.71 (d, 1H, J=15.9 Hz, CH=CH), 7.83 (d, 2H, J=8.4 Hz, ArH), 7.93-7.96 (m, 2H, ArH), 13.10 (brs, 1H, COOH).

Methyl 4-((quinolin-3-ylamino)methyl)benzoate

Compound 3

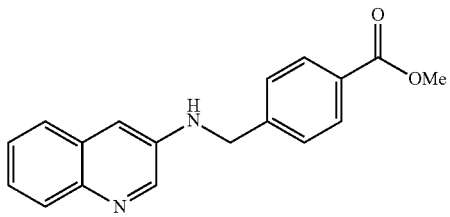

The title compound was obtained from 3-aminoquinoline (0.63 g, 4.25 mmol) according to Method A of Procedure A (1.2 g, 89%). $^1$H NMR (300 MHz, DMSO-d$_6$): δ 3.82 (s, 3H, OCH$_3$), 4.48 (d, 2H, J=6.0 Hz, CH$_2$), 6.94 (d, 1H, J=2.7 Hz, ArH), 6.98-7.03 (m, 1H, NH), 7.27-7.38 (m, 2H, ArH), 7.53-7.57 (m, 3H, ArH), 7.74-7.78 (m, 1H, ArH), 7.90-7.95 (m, 2H, ArH), 8.55 (d, 1H, J=2.7 Hz, ArH).

N-hydroxy-4-((quinolin-3-ylamino)methyl)benzamide

Compound 4

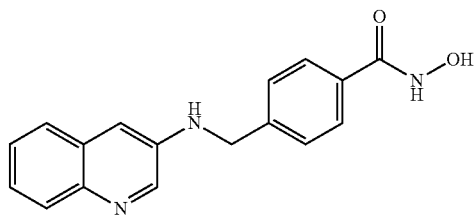

The title compound was obtained from the benzoate thus prepared (0.6 g, 2.05 mmol) according to Procedure C (0.56 g, 93%). $^1$H NMR (300 MHz, DMSO-d$_6$): δ 4.43 (d, 2H, J=5.7 Hz, CH$_2$), 6.93-6.98 (m, 2H, ArH), 7.27-7.38 (m, 2H, ArH), 7.67 (d, 2H, J=8.1 Hz, ArH), 7.54-7.58 (m, 1H, ArH), 7.69-7.78 (m, 3H, ArH), 8.54 (d, 1H, J=2.7 Hz, ArH). HRMS-ESI calcd. for C$_{17}$H$_{15}$N$_3$O$_2$ [M+H]$^+$ 294.1209, found 293.1164.

Example 2

(E)-methyl 3-(4-((quinolin-3-ylamino)methyl)phenyl)acrylate

Compound 5

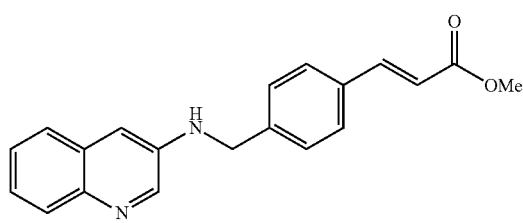

The title compound was obtained from 3-aminoquinoline (0.63 g, 4.25 mmol) according to Method A of Procedure A (1.2 g, 89%). $^1$H NMR (300 MHz, DMSO-d$_6$): δ 3.70 (s, 3H, OCH$_3$), 4.42 (d, 2H, J=6.0 Hz, CH$_2$), 6.59 (d, 1H, J=15.9 Hz, CH=CH), 6.93-6.97 (m, 2H, ArH, NH), 7.27-7.38 (m, 2H, ArH), 7.45 (d, 2H, J=8.1 Hz, ArH), 7.54-7.58 (m, 1H, ArH), 7.60-7.70 (m, 3H, ArH), 7.74-7.78 (m, 1H, ArH), 8.54 (d, 1H, J=2.1 Hz, ArH).

(E)-N-hydroxy-3-(4-((quinolin-3-ylamino)methyl)phenyl)acrylamide

Compound 6

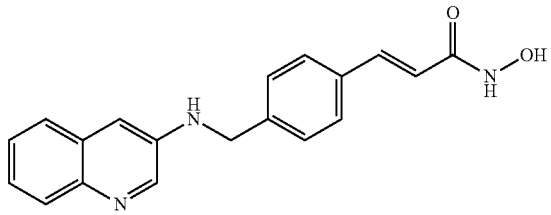

The title compound was obtained from the acrylate thus prepared (0.7 g, 2.2 mmol) according to Procedure C (0.61 g, 87%). $^1$H NMR (300 MHz, DMSO-d$_6$): δ 4.40 (d, 2H, J=5.7 Hz, CH$_2$), 6.42 (d, 1H, J=15.9 Hz, CH=CH), 6.91-6.97 (m, 2H, ArH, NH), 7.27-7.46 (m, 5H, ArH), 7.51-7.58 (m, 3H, ArH), 7.76 (d, 1H, J=7.8 Hz, ArH), 8.54 (d, 1H, J=2.7 Hz, ArH), 9.01 (s, 1H, NH), 10.73 (s, 1H, OH). HRMS-ESI calcd. for C$_{19}$H$_{17}$N$_3$O$_2$ [M+H]$^+$ 320.1365, found 319.1321.

Example 3

Methyl 4-(quinolin-3-ylcarbamoyl)benzoate

Compound 7

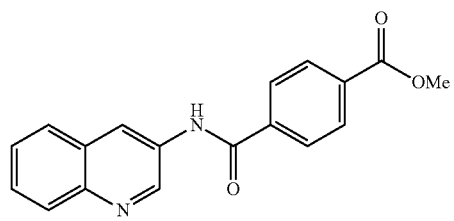

The title compound was obtained from 3-aminoquinoline (0.3 g, 2.04 mmol) and 4-dimethylaminopyridine (50 mg, 0.41 mmol) according to Method B of Procedure B (0.5 g, 80%). $^1$H NMR (300 MHz, DMSO-d$_6$): δ 3.90 (s, 3H, OCH$_3$), 7.56-7.62 (m, 1H, ArH), 7.64-7.71 (m, 1H, ArH), 7.95-8.00 (m, 2H, ArH), 8.10-8.18 (m, 4H, ArH), 8.85 (d, 1H, J=2.1 Hz, ArH), 9.14 (d, 1H, J=2.4 Hz, ArH), 10.89 (s, 1H, NH).

$N^1$-hydroxy-$N^4$-(quinolin-3-yl)terephthalamide

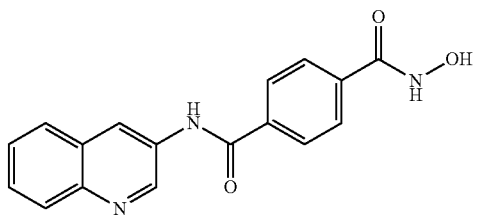

Compound 8

The title compound was obtained from the benzoate thus prepared (0.6 g, 1.96 mmol) according to Procedure C (0.55 g, 91%). $^1$H NMR (300 MHz, DMSO-$d_6$): δ 7.56-7.70 (m, 2H, ArH), 7.91-8.00 (m, 4H, ArH), 8.96 (d, 2H, J=8.4 Hz, ArH), 8.85 (d, 1H, J=2.1 Hz, ArH), 9.14 (d, 1H, J=2.4 Hz, ArH), 9.18 (s, 1H, NH), 10.79 (s, 1H, NH). 11.41 (s, 1H, OH).

Example 4

(E)-methyl 3-(4-(quinolin-3-ylcarbamoyl)phenyl)acrylate

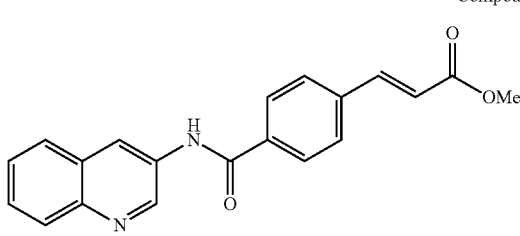

Compound 9

The title compound was obtained from 3-aminoquinoline (0.6 g, 4.08 mmol) and 4-dimethylaminopyridine (100 mg, 0.82 mmol) according to Method B of Procedure B (0.81 g, 59%). $^1$H NMR (300 MHz, DMSO-$d_6$): δ 3.75 (s, 3H, OCH$_3$), 6.81 (d, 1H, J=16.2 Hz, CH=CH), 7.56-7.62 (m, 1H, ArH), 7.64-7.70 (m, 1H, ArH), 7.75 (d, 1H, J=15.9 Hz, CH=CH), 7.91-8.00 (m, 4H, ArH), 8.07 (d, 2H, J=8.4 Hz, ArH), 8.85 (d, 1H, J=2.4 Hz, ArH), 9.14 (d, 1H, J=2.4 Hz, ArH), 10.75 (s, 1H, NH).

(E)-4-(3-(hydroxyamino)-3-oxoprop-1-enyl)-N-(quinolin-3-yl)benzamide

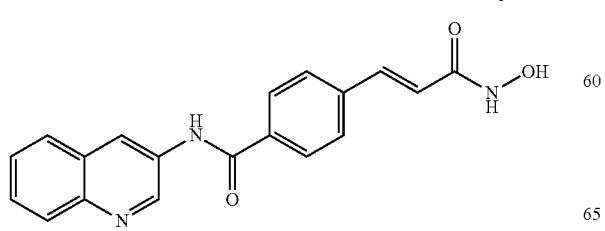

Compound 10

The title compound was obtained from the acrylate thus prepared (0.6 g, 1.81 mmol) according to Procedure C (0.56 g, 93%). $^1$H NMR (300 MHz, DMSO-$d_6$): δ 6.60 (d, 1H, J=15.9 Hz, CH=CH), 7.51-7.70 (m, 3H, ArH), 7.75 (d, 2H, J=8.1 Hz, ArH), 7.94-7.99 (m, 2H, ArH), 8.07 (d, 2H, J=8.4 Hz, ArH), 8.85 (d, 1H, J=2.4 Hz, ArH), 9.11-9.15 (m, 3H, ArH), 10.73 (s, 1H, NH), 10.85 (s, 1H, OH). HRMS-ESI calcd. for $C_{19}H_{15}N_3O_3$ [M+H]$^+$ 334.1175, found 333.1113.

Example 5

Methyl 4-((quinolin-5-ylamino)methyl)benzoate

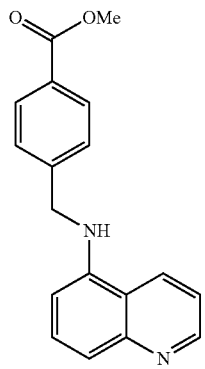

Compound 11

The title compound was obtained from 5-aminoquinoline (0.63 g, 4.25 mmol) according to Method A of Procedure A (1.15 g, 93%). $^1$H NMR (300 MHz, DMSO-$d_6$): δ 3.81 (s, 3H, OCH$_3$), 4.58 (d, 2H, J=6.0 Hz, CH$_2$), 6.34 (d, 1H, J=7.8 Hz, ArH), 7.19 (d, 1H, J=8.4 Hz, ArH), 7.28 (t, 1H, J=6.0 Hz, NH), 7.34-7.40 (m, 1H, ArH), 7.43 (dd, 1H, J=1.2, 8.4 Hz, ArH), 7.53 (d, 2H, J=8.1 Hz, ArH), 7.91 (d, 2H, J=8.4 Hz, ArH), 8.69 (d, 1H, J=8.1 Hz, ArH), 8.80 (dd, 1H, J=1.5, 4.2 Hz, ArH).

N-hydroxy-4-((quinolin-5-ylamino)methyl)benzamide

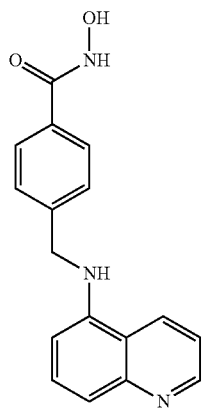

Compound 12

The title compound was obtained from the benzoate thus prepared (1.12 g, 3.83 mmol) according to Procedure C (1.02 g, 91%). $^1$H NMR (300 MHz, DMSO-$d_6$): δ 4.54 (d, 2H, J=5.7 Hz, CH$_2$), 6.37 (d, 1H, J=7.5 Hz, ArH), 7.18 (d, 1H, J=8.4 Hz, ArH), 7.24 (t, 1H, J=6.0 Hz, NH), 7.34-7.48

(m, 4H, ArH), 7.69 (d, 2H, J=8.4 Hz, ArH), 8.69 (d, 1H, J=8.4 Hz, ArH), 8.80 (dd, 1H, J=1.5, 4.2 Hz, ArH), 9.00 (s, 1H, NH), 11.14 (s, 1H, OH).

Example 6

(E)-methyl 3-(4-((quinolin-5-ylamino)methyl)phenyl)acrylate

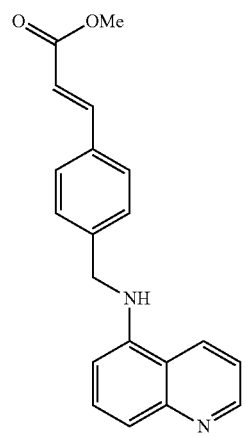

Compound 13

The title compound was obtained from 5-aminoquinoline (0.55 g, 3.7 mmol) according to Method A of Procedure A (0.95 g, 81%). $^1$H NMR (300 MHz, DMSO-d$_6$): δ 3.70 (s, 3H, OCH$_3$), 4.52 (d, 2H, J=6.0 Hz, CH$_2$), 6.38 (d, 1H, J=7.2 Hz, ArH), 6.57 (d, 1H, J=16.2 Hz, CH=CH), 7.18 (d, 1H, J=8.4 Hz, ArH), 7.23 (t, 1H, J=6.0 Hz, NH), 7.34-7.45 (m, 4H, ArH), 7.59-7.67 (m, 3H, ArH), 8.69 (d, 1H, J=8.4 Hz, ArH), 8.80 (d, 1H, J=1.5, 4.2 Hz, ArH).

(E)-N-hydroxy-3-(4-((quinolin-5-ylamino)methyl)phenyl)acrylamide

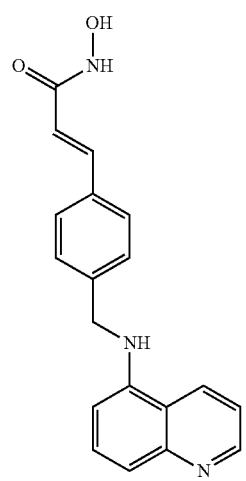

Compound 14

The title compound was obtained from the acrylate thus prepared (0.86 g, 2.7 mmol) according to Procedure C (0.83 g, 96%). $^1$H NMR (300 MHz, DMSO-d$_6$): δ 4.51 (d, 2H, J=6.0 Hz, CH$_2$), 6.36-6.43 (m, 2H, ArH), 7.15-7.24 (m, 2H, ArH), 7.37-7.45 (m, 5H, ArH), 7.50 (d, 2H, J=8.1 Hz, ArH), 8.69 (d, 1H, J=8.4 Hz, ArH), 8.78-8.81 (m, 1H, ArH), 9.01 (s, 1H, NH), 10.72 (s, 1H, OH). HRMS-ESI calcd. for C$_{19}$H$_{17}$N$_3$O$_2$ [M+H]$^+$ 320.1375, found 319.1321.

Example 7

Methyl 4-(quinolin-5-ylcarbamoyl)benzoate

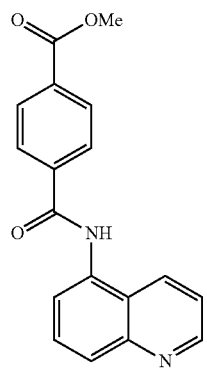

Compound 15

The title compound was obtained from 5-aminoquinoline (4 g, 27.8 mmol) according to Method A of Procedure B (0.75 g, 9%). $^1$H NMR (300 MHz, DMSO-d$_6$): δ 3.91 (s, 3H, OCH$_3$), 7.56 (dd, 1H, J=1.2, 8.4 Hz, ArH), 7.70-7.73 (m, 1H, ArH), 7.77-7.83 (m, 1H, ArH), 7.97 (d, 1H, J=8.1 Hz, ArH), 8.13 (d, 2H, J=8.4 Hz, ArH), 8.21 (d, 2H, J=8.4 Hz, ArH), 8.41 (d, 2H, J=8.7 Hz, ArH), 8.92-8.95 (m, 1H, ArH), 10.73 (s, 1H, NH).

N$_1$-hydroxy-N$_4$-(quinolin-5-yl)terephthalamide

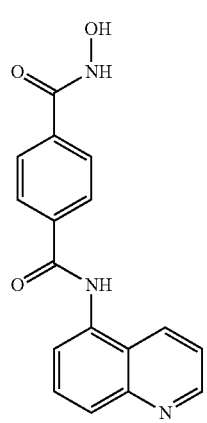

Compound 16

The title compound was obtained from the benzoate thus prepared (0.6 g, 1.96 mmol) according to Procedure C (0.56 g, 93%). $^1$H NMR (300 MHz, DMSO-d$_6$): δ 7.55 (dd, 1H, J=4.2 Hz, ArH), 7.70-7.73 (m, 1H, ArH), 7.77-7.83 (m, 1H, ArH), 7.90-7.98 (m, 3H, ArH), 8.14 (d, 2H, J=8.4 Hz, ArH), 8.41 (d, 1H, J=8.1 Hz, ArH), 8.93 (dd, 1H, J=1.5, 4.2 Hz, NH), 9.17 (s, 1H, NH), 10.64 (s, 1H, NH), 11.41 (s, 1H, OH). HRMS-ESI calcd. for C$_{17}$H$_{13}$N$_3$O$_3$ [M+H]$^+$ 308.1004, found 307.0957.

Example 8

(E)-methyl 3-(4-(quinolin-5-ylcarbamoyl)phenyl) acrylate

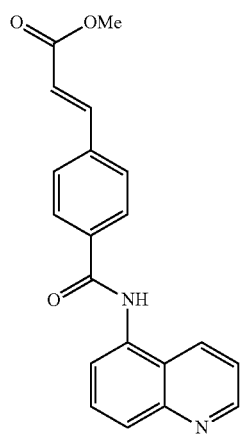

Compound 17

The title compound was obtained from 5-aminoquinoline (0.6 g, 4.1 mmol) according to Method B of Procedure B (1.02 g, 68%). $^1$H NMR (300 MHz, DMSO-d$_6$): δ 3.75 (s, 3H, OCH$_3$), 6.81 (d, 1H, J=16.2 Hz, CH=CH), 7.55 (dd, 1H, J=1.2, 8.4 Hz, ArH), 7.70-7.83 (m, 3H, ArH), 7.90-7.98 (m, 3H, ArH), 8.12 (d, 2H, J=8.4 Hz, ArH), 8.40 (d, 1H, J=8.4 Hz, ArH), 8.93 (d, 1H, J=1.5, 3.9 Hz, ArH), 10.60 (s, 1H, NH).

(E)-4-(3-(hydroxyamino)-3-oxoprop-1-enyl)-N-(quinolin-5-yl)benzamide

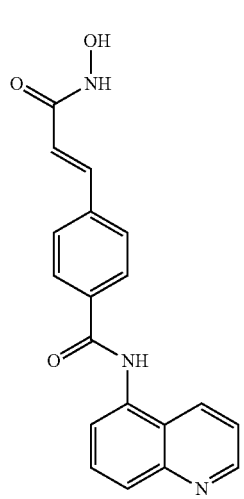

Compound 18

The title compound was obtained from the acrylate thus prepared (0.6 g, 1.81 mmol) according to Procedure C (0.54 g, 90%). $^1$H NMR (300 MHz, DMSO-d$_6$): δ 6.61 (d, 1H, J=15.9 Hz, CH=CH), 7.52-7.58 (m, 2H, ArH), 7.69-7.83 (m, 4H, ArH), 7.96 (d, 1H, J=8.1 Hz, ArH), 8.11 (d, 1H, J=8.4 Hz, ArH), 8.39 (d, 1H, J=8.1 Hz, ArH), 8.93 (dd, 1H, J=1.5, 4.2 Hz, ArH), 9.12 (s, 1H, NH), 10.58 (s, 1H, NH), 10.85 (s, 1H, OH). HRMS-ESI calcd. for C$_{19}$H$_{15}$N$_3$O$_3$ [M+H]$^+$ 334.1175, found 333.1113.

Example 9

Methyl 4-((quinolin-6-ylamino)methyl)benzoate

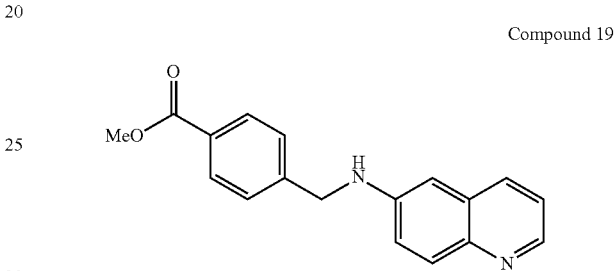

Compound 19

The title compound was obtained from 6-aminoquinoline (0.63 g, 4.25 mmol) according to Method A of Procedure A (1.05 g, 85%). $^1$H NMR (300 MHz, DMSO-d$_6$): δ 3.82 (s, 3H, OCH$_3$), 4.47 (d, 2H, J=6.0 Hz, CH$_2$), 6.62 (d, 1H, J=2.4 Hz, ArH), 6.86-6.91 (m, 1H, NH), 7.22-7.30 (m, 2H, ArH), 7.54 (d, 2H, J=9.0 Hz, ArH), 7.72 (d, 1H, J=9.0 Hz, ArH), 7.86-7.94 (m, 1H, ArH), 8.46 (dd, 1H, J=1.5, 4.2 Hz, ArH).

N-hydroxy-4-((quinolin-6-ylamino)methyl)benzamide

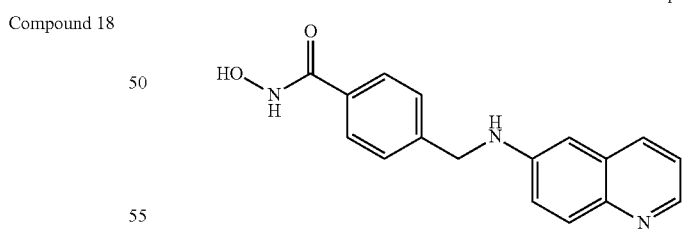

Compound 20

The title compound was obtained from the benzoate thus prepared (0.6 g, 2.05 mmol) according to Procedure C (0.56 g, 93%). $^1$H NMR (300 MHz, DMSO-d$_6$): δ 4.56 (d, 2H, J=5.7 Hz, CH$_2$), 6.62 (d, 1H, J=2.4 Hz, ArH), 6.88 (t, 1H, J=5.7 Hz, NH), 7.22-7.30 (m, 2H, ArH), 7.51 (d, 2H, J=8.1 Hz, ArH), 7.71 (d, 1H, J=9.0 Hz, ArH), 7.88-7.92 (m, 3H, ArH), 8.46 (dd, 1H, J=1.5, 4.2 Hz, ArH). HRMS-ESI calcd. for C$_{17}$H$_{15}$N$_3$O$_2$ [M−H]$^+$ 292.1069, found 293.1164.

Example 10

(E)-methyl 3-(4-((quinolin-6-ylamino)methyl)phenyl)acrylate

Compound 21

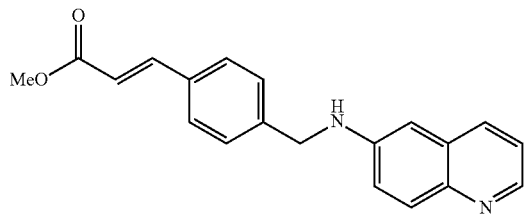

The title compound was obtained from 6-aminoquinoline (0.63 g, 4.25 mmol) according to Method A of Procedure A (1.11 g, 82%). $^1$H NMR (300 MHz, DMSO-$d_6$): δ 3.70 (s, 3H, OCH$_3$), 4.41 (d, 2H, J=6.0 Hz, CH$_2$), 6.59 (d, 1H, J=16.2 Hz, CH=CH), 6.64 (d, 1H, J=2.4 Hz, ArH), 6.83 (t, 1H, J=6.0 Hz, NH), 7.22-7.29 (m, 2H, ArH), 7.44 (d, 2H, J=8.1 Hz, ArH), 7.60-7.73 (m, 4H, ArH), 7.89 (dd, 1H, J=0.9, 8.4 Hz, ArH), 8.46 (dd, 1H, J=1.5, 4.2 Hz, ArH).

(E)-N-hydroxy-3-(4-((quinolin-6-ylamino)methyl)phenyl)acrylamide

Compound 22

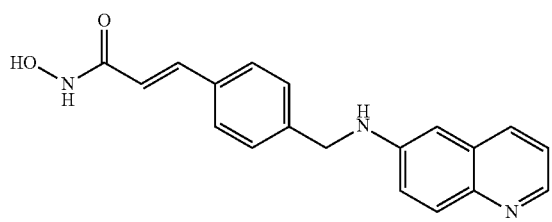

The title compound was obtained from the acrylate thus prepared (0.6 g, 1.88 mmol) according to Procedure C (0.55 g, 92%). $^1$H NMR (300 MHz, DMSO-$d_6$): δ 4.40 (d, 2H, J=5.7 Hz, CH$_2$), 6.48 (d, 1H, J=15.9 Hz, CH=CH), 6.64 (d, 1H, J=2.4 Hz, ArH), 6.82 (t, 1H, J=5.7 Hz, NH), 7.22-7.28 (m, 2H, ArH), 7.43 (d, 2H, J=8.1 Hz, ArH), 7.54 (d, 1H, J=16.2 Hz, CH=CH), 7.60-7.72 (m, 3H, ArH), 7.89 (d, 1H, J=8.1 Hz, ArH), 8.45 (d, 1H, J=2.7 Hz, ArH). HRMS-ESI calcd. for $C_{19}H_{17}N_3O_2$ [M+H]$^+$ 320.1409, found 319.1321.

Example 11

Methyl 4-(quinolin-6-ylcarbamoyl)benzoate

Compound 23

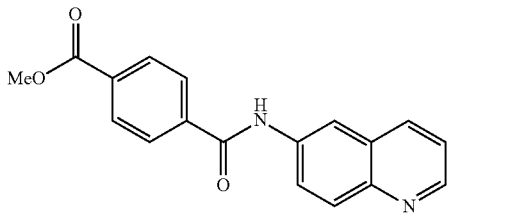

The title compound was obtained from 6-aminoquinoline (2 g, 13.6 mmol) according to Method A of Procedure B (1.2 g, 29%). $^1$H NMR (300 MHz, DMSO-$d_6$): δ 3.89 (s, 3H, OCH$_3$), 7.50 (dd, 1H, J=4.2 Hz, ArH), 8.02-8.04 (m, 2H, ArH), 8.09-8.13 (m, 4H, ArH), 8.34 (dd, 1H, J=1.8, 8.1 Hz, ArH), 8.53-8.55 (m, 1H, ArH), 8.81 (dd, 1H, J=1.8, 4.2 Hz, ArH), 10.78 (s, 1H, NH).

$N^1$-hydroxy-$N^4$-(quinolin-6-yl)terephthalamide

Compound 24

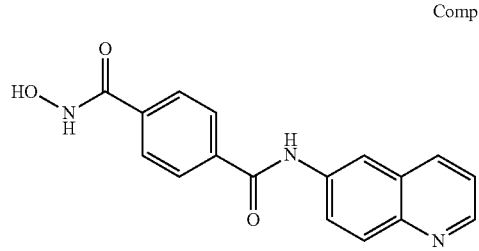

The title compound was obtained from the benzoate thus prepared (0.6 g, 1.96 mmol) according to Procedure C (0.12 g, 20%). $^1$H NMR (300 MHz, DMSO-$d_6$): δ 7.49 (dd, 1H, J=4.2 Hz, ArH), 7.91 (d, 2H, J=8.1 Hz, ArH), 7.98-8.09 (m, 4H, ArH), 8.33 (d, 1H, J=8.1 Hz, ArH), 8.55 (s, 1H, ArH), 8.81 (d, 1H, J=3.0 Hz, ArH), 9.19 (s, 1H, NH), 10.67 (s, 1H, NH), 11.42 (s, 1H, OH). HRMS-ESI calcd. for $C_{17}H_{13}N_3O_3$ [M+H]$^+$ 308.1005, found 307.0957.

Example 12

(E)-methyl 3-(4-(quinolin-6-ylcarbamoyl)phenyl)acrylate

Compound 25

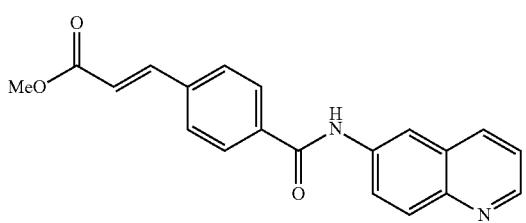

The title compound was obtained from 6-aminoquinoline (0.6 g, 4.08 mmol) according to Method B of Procedure B (0.7 g, 52%). $^1$H NMR (300 MHz, DMSO-d$_6$): δ 3.75 (s, 3H, OCH$_3$), 6.80 (d, 1H, J=16.2 Hz, CH=CH), 7.50 (dd, 1H, J=4.2 Hz, ArH), 7.74 (d, 1H, J=15.9 Hz, CH=CH), 7.91 (d, 2H, J=8.7 Hz, ArH), 7.98-8.07 (m, 4H, ArH), 8.32 (dd, 1H, J=1.2, 8.4 Hz, ArH), 8.54 (d, 1H, J=1.8 Hz, ArH), 8.80 (dd, 1H, J=1.5, 4.2 Hz, ArH), 10.62 (s, 1H, NH).

(E)-4-(3-(hydroxyamino)-3-oxoprop-1-enyl)-N-(quinolin-6-yl)benzamide

Compound 26

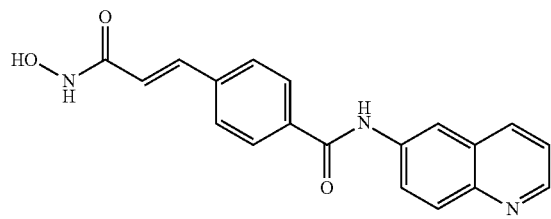

The title compound was obtained from the acrylate thus prepared (0.5 g, 1.51 mmol) according to Procedure C (0.46 g, 91%). $^1$H NMR (300 MHz, DMSO-d$_6$): δ 6.60 (d, 1H, J=15.9 Hz, CH=CH), 7.47-7.56 (m, 2H, ArH), 7.74 (d, 2H, J=8.4 Hz, ArH), 7.98-8.07 (m, 4H, ArH), 8.32 (dd, 1H, J=1.2, 8.4 Hz, ArH), 8.53 (d, 1H, J=1.8 Hz, ArH), 8.80 (dd, 1H, J=1.5, 4.2 Hz, ArH), 10.61 (s, 1H, NH). HRMS-ESI calcd. for C$_{19}$H$_{15}$N$_3$O$_3$ [M+H]$^+$ 334.1162, found 333.1113.

Example 13

Methyl 4-((quinolin-8-ylamino)methyl)benzoate

Compound 27

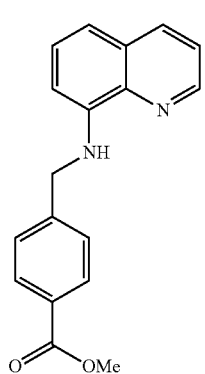

The title compound was obtained from 8-aminoquinoline (0.63 g, 4.25 mmol) according to Method A of Procedure A (1.12 g, 90%). $^1$H NMR (300 MHz, DMSO-d$_6$): δ 3.81 (s, 3H, OCH$_3$), 4.62 (d, 2H, J=6.3 Hz, CH$_2$), 6.46-6.50 (m, 1H, ArH), 7.04 (dd, 1H, J=0.9, 8.1 Hz, ArH), 7.21-7.32 (m, 2H, ArH, NH), 7.47-7.53 (m, 3H, ArH), 7.89 (d, 2H, J=8.4 Hz, ArH), 8.17-8.21 (m, 1H, ArH), 8.76 (dd, 1H, J=1.8, 4.2 Hz, ArH).

N-hydroxy-4-((quinolin-8-ylamino)methyl)benzamide

Compound 28

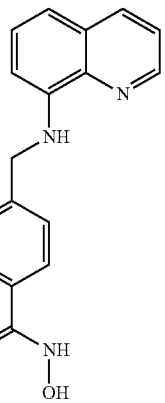

The title compound was obtained from the benzoate thus prepared (1.12 g, 3.83 mmol) according to Procedure C (1.03 g, 92%). $^1$H NMR (300 MHz, DMSO-d$_6$): δ 4.57 (d, 2H, J=6.3 Hz, CH$_2$), 6.51 (dd, 1H, J=1.2, 7.8 Hz, ArH), 7.04 (dd, 1H, J=1.2, 8.4 Hz, NH), 7.21-7.28 (m, 2H, ArH), 7.45 (d, 2H, J=8.1 Hz, ArH), 7.50 (dd, 1H, J=4.2, 8.4 Hz, ArH), 7.68 (d, 2H, J=8.1 Hz, ArH), 8.20 (dd, 1H, J=1.8, 8.4 Hz, ArH), 8.76 (dd, 1H, J=1.8, 4.2 Hz, ArH), 8.96 (brs, 1H, NH), 11.11 (brs, 1H, OH). HRMS-ESI calcd. for C$_{17}$H$_{15}$N$_3$O$_2$ [M+H]$^+$ 294.1217, found 293.1164.

Example 14

(E)-methyl 3-(4-((quinolin-8-ylamino)methyl)phenyl)acrylate

Compound 29

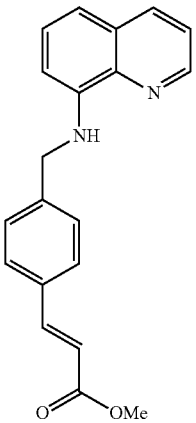

The title compound was obtained from 8-aminoquinoline (0.7 g, 4.76 mmol) according to Method A of Procedure A (1.36 g, 90%). $^1$H NMR (300 MHz, DMSO-d$_6$): δ 3.70 (s, 3H, OCH$_3$), 4.53 (d, 2H, J=5.7 Hz, CH$_2$), 6.38 (d, 1H, J=7.8 Hz, ArH), 6.58 (d, 1H, J=16.2 Hz, CH=CH), 7.17-7.25 (m, 2H, NH, ArH), 7.35-7.43 (m, 4H, ArH), 7.44-7.67 (m, 3H, ArH), 8.70 (d, 1H, J=8.7 Hz, ArH), 8.79-8.81 (m, 1H, ArH).

25
(E)-N-hydroxy-3-(4-((quinolin-8-ylamino)methyl)phenyl)acrylamide

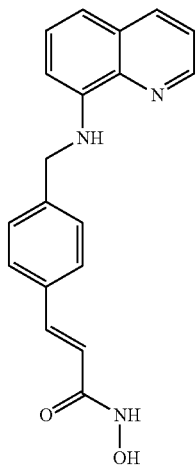

Compound 30

The title compound was obtained from the acrylate thus prepared (1.36 g, 4.47 mmol) according to Procedure C (1.26 g, 88%). $^1$H NMR (300 MHz, DMSO-$d_6$): δ 4.55 (d, 2H, J=6.6 Hz, CH$_2$), 6.40 (d, 1H, J=15.6 Hz, CH=CH), 6.53 (dd, 1H, J=0.9, 7.5 Hz, ArH), 7.02-7.06 (m, 1H, ArH), 7.19-7.29 (m, 2H, ArH), 7.38-7.53 (m, 6H, ArH), 8.20 (dd, 1H, J=1.8, 8.4 Hz, ArH), 8.76 (dd, 1H, J=1.5, 4.2 Hz, ArH), 8.99 (brs, 1H, NH), 10.72 (brs, 1H, OH). HRMS-ESI calcd. for C$_{19}$H$_{17}$N$_3$O$_2$ [M+H]$^+$ 320.1382, found 319.1321.

Example 15

Methyl 4-(quinolin-8-ylcarbamoyl)benzoate

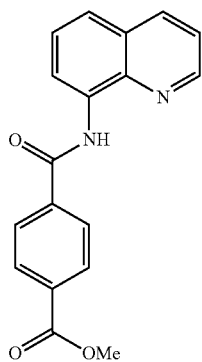

Compound 31

The title compound was obtained from 8-aminoquinoline (2 g, 13.6 mmol) according to Method A of Procedure A (3.6 g, 86%). $^1$H NMR (300 MHz, DMSO-$d_6$): δ 3.90 (s, 3H, OCH$_3$), 7.61-7.69 (m, 2H, ArH), 7.73-7.77 (m, 1H, ArH), 8.14 (s, 4H, ArH), 8.44 (dd, 1H, J=1.5, 8.4 Hz, ArH), 8.70 (dd, 1H, J=1.5, 7.5 Hz, ArH), 8.96 (dd, 1H, J=1.8, 4.2 Hz, ArH), 10.70 (s, 1H, NH).

26
N$^1$-hydroxy-N$^4$-(quinolin-8-yl)terephthalamide

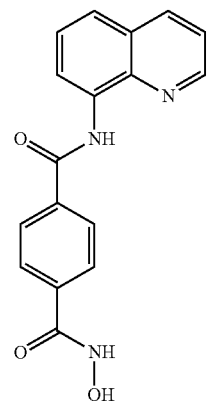

Compound 32

The title compound was obtained from the benzoate thus prepared (0.6 g, 1.96 mmol) according to Procedure C (0.53 g, 88%). $^1$H NMR (300 MHz, DMSO-$d_6$): δ 7.61-7.77 (m, 3H, ArH), 7.95-8.16 (m, 4H, ArH), 8.45 (d, 1H, J=8.4 Hz, ArH), 8.69-8.75 (m, 1H, ArH), 8.97 (d, 1H, J=3.6 Hz, ArH), 10.68 (s, 1H, NH). HRMS-ESI calcd. for C$_{17}$H$_{13}$N$_3$O$_3$ [M+H]$^+$ 308.1016, found 307.0957.

Example 16

(E)-methyl 3-(4-(quinolin-8-ylcarbamoyl)phenyl)acrylate

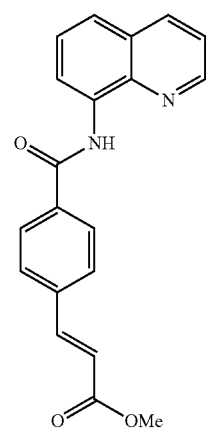

Compound 33

The title compound was obtained from 8-aminoquinoline (0.7 g, 4.76 mmol) according to Method B of Procedure B (0.75 g, 47%). $^1$H NMR (500 MHz, CDCl$_3$): δ 3.84 (s, 3H, OCH$_3$), 6.55 (d, 1H, J=16.0 Hz, CH=CH), 6.50 (dd, 1H, J=4.0, 8.5 Hz), 7.56-7.63 (m, 2H, ArH), 7.70 (d, 2H, J=8.0 Hz, ArH), 7.76 (d, 1H, J=16.0 Hz, CH=CH), 8.11 (d, 2H, J=8.0 Hz, CH=CH), 8.20 (dd, 1H, J=1.0, 8.0 Hz, ArH), 8.86 (dd, 1H, J=1.5, 4 Hz, ArH), 8.93 (d, 1H, J=7.5 Hz, ArH), 10.78 (s, 1H, NH).

(E)-4-(3-(hydroxyamino)-3-oxoprop-1-enyl)-N-(quinolin-8-yl)benzamide

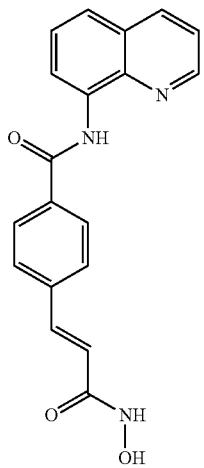

Compound 34

The title compound was obtained from the acrylate thus prepared (0.6 g, 1.8 mmol) according to Procedure C (0.53 g, 89%). $^1$H NMR (300 MHz, DMSO-$d_6$): δ 6.60 (d, 1H, J=15.9 Hz, CH=CH), 7.55 (d, 1H, J=16.2 Hz, CH=CH), 7.63-7.81 (m, 5H, ArH), 8.06 (d, 2H, J=8.4 Hz, ArH), 8.45-8.48 (m, 1H, ArH), 8.71-8.74 (m, 1H, ArH), 8.97-8.99 (m, 1H, ArH), 9.12 (brs, 1H, NH), 10.68 (s, 1H, NH), 10.87 (brs, 1H, OH). HRMS-ESI calcd. for $C_{19}H_{15}N_3O_3$ [M+H]$^+$ 334.1180, found 333.1113.

Example 17

Methyl 3-((quinolin-8-ylamino)methyl)benzoate

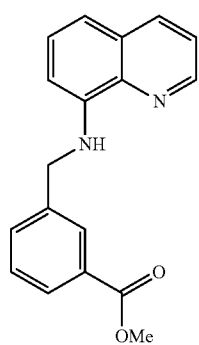

Compound 35

$^1$H NMR (300 MHz, $d_6$-DMSO): δ 3.80 (s, 3H, OCH$_3$), 4.60 (d, 2H, J=6.3 Hz, CH$_2$), 6.49-6.53 (m, 1H, ArH), 7.03 (dd, 1H, J=1.2, 8.1 Hz, ArH), 7.25 (t, 1H, J=7.8 Hz, ArH), 7.28-7.34 (m, 1H, NH), 7.43-7.53 (m, 2H, ArH), 7.66-7.70 (m, 1H, ArH), 7.79-7.83 (m, 1H, ArH), 8.00-8.12 (m, 1H, ArH), 8.18-8.22 (m, 1H, ArH), 8.77 (dd, 1H, J=1.8, 4.2 Hz, ArH).

N-hydroxy-3-((quinolin-8-ylamino)methyl)benzamide

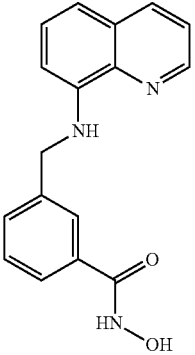

Compound 36

$^1$H NMR (300 MHz, $d_6$-DMSO): δ 4.57 (d, 2H, J=6.3 Hz, CH$_2$), 6.54 (d, 1H, J=7.2, 8.1 Hz, ArH), 7.04 (d, 1H, J=7.5 Hz, ArH), 7.19-7.29 (m, 2H, ArH), 7.34-7.40 (m, 1H, NH), 7.47-7.60 (m, 3H, ArH), 7.82 (s, 1H, ArH), 8.17-8.22 (m, 1H, ArH), 8.75-8.77 (m, 1H, ArH), 8.99 (s, 1H, NH), 11.19 (s, 1H, OH). HRMS-ESI calcd. for $C_{17}H_{15}N_3O_2$ [M+H]$^+$ 294.1209, found 293.1164.

Example 18

Methyl 3-(quinolin-8-ylcarbamoyl)benzoate

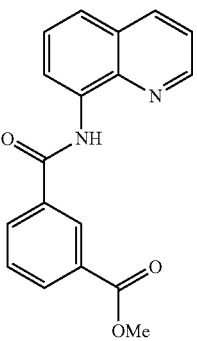

Compound 37

$^1$H NMR (300 MHz, $d_6$-DMSO): δ 3.92 (s, 3H, OCH$_3$), 7.62-7.69 (m, 2H, ArH), 7.74-7.79 (m, 2H, ArH), 8.18-8.22 (m, 1H, ArH), 8.28-8.31 (m, 1H, ArH), 8.43-8.47 (m, 1H, ArH), 8.54-8.56 (m, 1H, ArH), 8.69 (dd, 1H, J=1.2, 7.5 Hz, ArH), 8.97 (dd, 1H, J=1.5, 4.2 Hz, ArH), 10.72 (s, 1H, NH).

M-hydroxy-N³-(quinolin-8-yl)isophthalamide

Compound 38

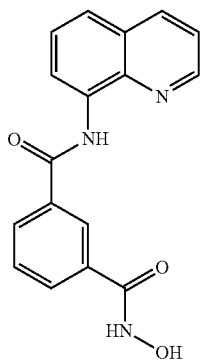

¹H NMR (300 MHz, d₆-DMSO): δ 7.63-7.78 (m, 4H, ArH), 8.01 (d, 1H, J=7.8 Hz, ArH), 8.17 (d, 1H, J=7.8 Hz, ArH), 8.41 (s, 1H, ArH), 8.44-8.48 (m, 1H, ArH), 8.70-8.74 (m, 1H, ArH), 8.98 (dd, 1H, J=1.5, 4.2 Hz, ArH), 9.20 (s, 1H, NH), 10.68 (s, 1H, NH), 11.46 (s, 1H, OH). HRMS-ESI calcd. for $C_{17}H_{13}N_3O_3$ [M+H]⁺ 308.1008, found 307.0957.

Example 19

Methyl 4-((quinolin-2-ylamino)methyl)benzoate

Compound 39

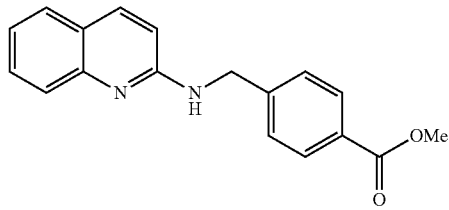

¹H NMR (300 MHz, d₆-DMSO): δ 3.82 (s, 3H, OCH₃), 4.72 (d, 2H, J=6.0 Hz, CH₂), 6.84 (d, 1H, J=9.0 Hz, ArH), 7.10-7.17 (m, 1H, ArH), 7.40-7.48 (m, 2H, ArH, NH), 7.52 (d, 1H, J=8.4 Hz, ArH), 7.59-7.64 (m, 2H, ArH), 7.85-7.93 (m, 3H, ArH).

N-hydroxy-4-((quinolin-2-ylamino)methyl)benzamide

Compound 40

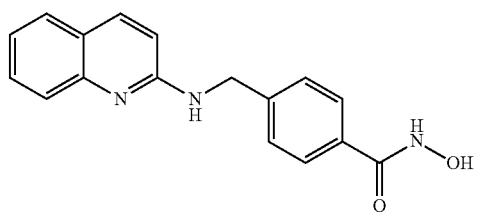

¹H NMR (300 MHz, d₆-DMSO): δ 4.67 (d, 2H, J=5.7 Hz, CH₂), 6.83 (d, 1H, J=9.0 Hz, ArH), 7.10-7.17 (m, 1H, ArH), 7.42-7.46 (m, 4H, ArH, NH), 7.54-7.62 (m, 2H, ArH), 7.69 (d, 2H, J=8.1 Hz, ArH), 7.87 (d, 1H, J=9.0 Hz, ArH), 8.98 (s, 1H, NH), 11.14 (s, 1H, OH). HRMS-ESI calcd. for $C_{17}H_{15}N_3O_2$ [M+H]⁺ 294.1208, found 293.1164.

Example 20

Methyl 4-((quinolin-7-ylamino)methyl)benzoate

Compound 41

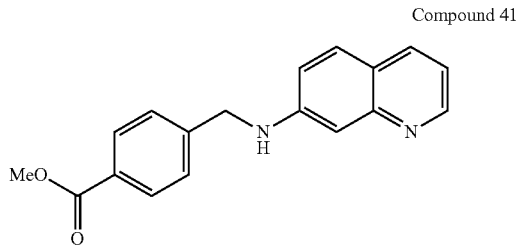 [SMILES: COC(=O)c1ccc(CNc2ccc3cccnc3c2)cc1]

¹H NMR (300 MHz, d₆-DMSO): δ 3.82 (s, 3H, OCH₃), 4.50 (d, 2H, J=6.0 Hz, CH₂), 6.68 (d, 1H, J=2.4 Hz, ArH), 7.02-7.13 (m, 3H, ArH, NH), 7.54 (d, 2H, J=8.4 Hz, ArH), 7.63 (d, 1H, J=9.0 Hz, ArH), 7.93 (dt, 2H, J=1.8, 8.4 Hz, ArH), 7.98-8.02 (m, 1H, ArH), 8.55 (dd, 1H, J=1.8, 4.2 Hz, ArH).

N-hydroxy-4-((quinolin-7-ylamino)methyl)benzamide

Compound 42

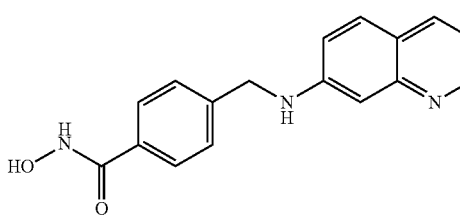

¹H NMR (300 MHz, d₆-DMSO): δ 4.45 (d, 2H, J=5.7 Hz, CH₂), 6.70 (d, 1H, J=2.1 Hz, ArH), 6.99-7.14 (m, 3H, ArH, NH), 7.47 (d, 2H, J=8.1 Hz, ArH), 7.62 (d, 1H, J=8.7 Hz, ArH), 7.71 (d, 2H, J=8.4 Hz, ArH), 8.00 (dd, 1H, J=1.2, 8.0 Hz, ArH), 8.54-8.57 (m, 1H, ArH), 9.02 (s, 1H, NH), 11.15 (s, 1H, OH). HRMS-ESI calcd. for $C_{17}H_{15}N_3O_2$ [M+H]⁺ 294.1222, found 293.1164.

Example 21

Methyl 4-((quinolin-4-ylamino)methyl)benzoate

Compound 43

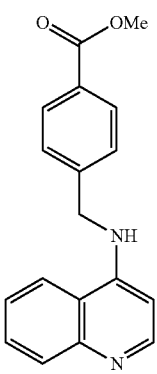

$^1$H NMR (300 MHz, d$_6$-DMSO): δ 3.81 (s, 3H, OCH$_3$), 4.63 (d, 2H, J=6.0 Hz, CH$_2$), 6.27 (d, 1H, J=5.4 Hz, ArH), 7.43-7.53 (m, 3H, ArH), 7.59-7.65 (m, 1H, ArH), 7.77-7.81 (m, 1H, ArH), 7.89-7.93 (m, 2H, ArH), 7.97 (t, 1H, J=6.0 Hz, NH), 8.27-8.31 (m, 2H, ArH).

N-hydroxy-4-((quinolin-4-ylamino)methyl)benzamide

Compound 44

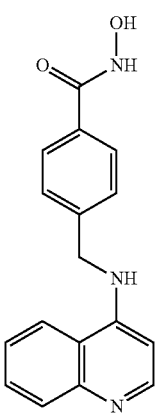

$^1$H NMR (300 MHz, d$_6$-DMSO): δ 4.59 (d, 2H, J=5.1 Hz, CH$_2$), 6.29 (d, 1H, J=5.4 Hz, ArH), 7.42-7.48 (m, 3H, ArH), 7.59-7.65 (m, 1H, ArH), 7.69 (d, 2H, J=8.1 Hz, ArH), 7.78 (d, 1H, J=8.4 Hz, ArH), 7.95 (s, 1H, NH), 8.29 (d, 1H, J=5.4 Hz, ArH). HRMS-ESI calcd. for C$_{17}$H$_{15}$N$_3$O$_2$ [M+H]$^+$ 294.1243, found 294.1209.

Example 22

Quinolin-8-ylmethanamine

Compound 45

$^1$H NMR (300 MHz, CDCl$_3$): δ 2.55 (brs, 2H, NH$_2$), 4.29 (s, 2H, CH$_2$), 7.21-7.36 (m, 2H, ArH), 7.47-7.58 (m, 2H, ArH), 7.98 (d, 1H, J=7.2 Hz, ArH), 8.77 (d, 1H, J=2.1 Hz, ArH).

Methyl 4-((quinolin-8-ylmethyl)carbamoyl)benzoate

Compound 46

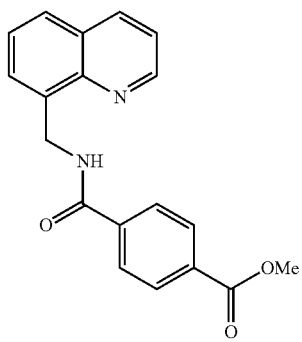

$^1$H NMR (300 MHz, d$_6$-DMSO): δ 3.88 (s, 3H, OCH$_3$), 5.15 (d, 2H, J=6.0 Hz, CH$_2$), 7.54-7.61 (m, 2H, ArH), 7.63-7.67 (m, 1H, ArH), 7.87-7.91 (m, 1H, ArH), 8.03-8.10 (m, 4H, ArH), 8.39 (dd, 1H, J=1.8, 8.4 Hz, ArH), 8.97 (dd, 1H, J=1.8, 4.2 Hz, ArH), 9.23-9.28 (m, 1H, NH).

N$^1$-hydroxy-N$^4$-(quinolin-8-ylmethyl)terephthalamide

Compound 47

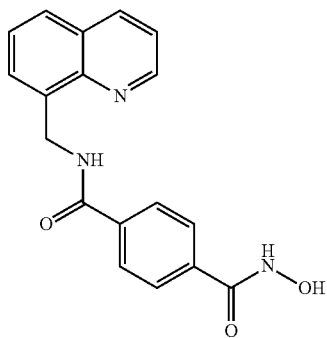

¹H NMR (300 MHz, d₆-DMSO): δ 5.15 (d, 2H, J=6.0 Hz, CH₂), 7.54-7.66 (m, 3H, ArH), 7.83-7.90 (m, 3H, ArH), 8.01 (d, 2H, J=8.4 Hz, ArH), 8.39 (dd, 1H, J=1.8, 8.4 Hz, ArH), 8.97 (dd, 1H, J=1.8, 4.2 Hz, ArH), 9.13-9.20 (m, 2H, NH), 11.35 (s, 1H, OH). HRMS-ESI calcd. for $C_{18}H_{15}N_3O_3$ [M+H]⁺ 322.1192, found 322.1170.

Example 23

4-(2-ethoxy-2-oxoethyl)benzoic acid

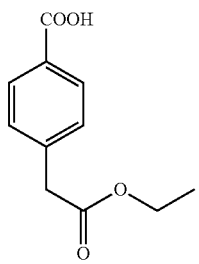

Compound 48

¹H NMR (300 MHz, CDCl₃): δ 1.26 (t, 3H, J=7.2 Hz, CH₃), 3.69 (s, 2H, CH₂), 4.17 (q, 2H, J=7.2 Hz, CH₂), 7.40 (d, 2H, J=8.4 Hz, ArH), 8.08 (d, 2H, J=8.1 Hz, ArH).

Ethyl 2-(4-(quinolin-8-ylcarbamoyl)phenyl)acetate

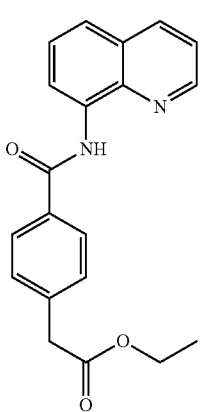

Compound 49

¹H NMR (300 MHz, CDCl₃): δ 1.24-2.30 (m, 3H, CH₃), 3.71 (s, 2H, CH₂), 4.14-4.22 (m, 2H, CH₂), 7.44-7.49 (m, 3H, ArH), 7.51-7.62 (m, 2H, ArH), 8.02-8.07 (m, 2H, ArH), 8.15-8.20 (m, 1H, ArH), 8.84 (dd, 1H, J=1.8, 4.2 Hz, ArH), 8.90-8.94 (m, 1H, ArH), 10.72 (s, 1H, NH).

4-(2-(hydroxyamino)-2-oxoethyl)-N-(quinolin-8-yl)benzamide

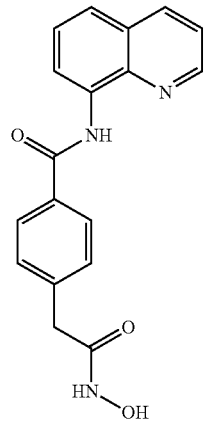

Compound 50

¹H NMR (300 MHz, d₆-DMSO): δ 3.41 (s, 2H, CH₂), 7.49 (d, 2H, J=8.1 Hz, ArH), 7.62-7.75 (m, 3H, ArH), 7.97 (d, 2H, J=8.4 Hz, ArH), 8.45 (dd, 1H, J=1.5, 8.4 Hz, ArH), 8.72 (dd, 1H, J=1.2, 7.5 Hz, ArH), 8.89 (d, 1H, J=1.5 Hz, NH), 8.97 (dd, 1H, J=1.5, 4.2 Hz, ArH), 10.62 (s, 1H, NH), 10.72 (s, 1H, NH). HRMS-ESI calcd. for $C_{18}H_{15}N_3O_3$ [M+H]⁺ 322.1192, found 322.1163.

Example 24

Methyl 4-(2-(quinolin-8-yl)ethyl)benzoate

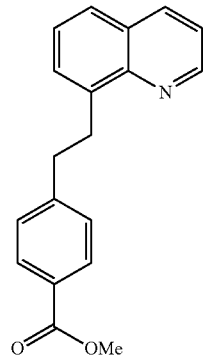

Compound 51

¹H NMR (300 MHz, CDCl₃): δ 3.16-3.22 (m, 2H, CH₂), 3.58-3.64 (m, 2H, CH₂), 3.91 (s, 3H, OCH₃), 7.29 (d, 1H, J=8.4 Hz, ArH), 7.38-7.44 (m, 3H, ArH), 7.66-7.72 (m, 1H, ArH), 7.94-8.00 (m, 2H, ArH), 8.15 (dd, 1H, J=1.8, 8.4 Hz, ArH), 8.97 (dd, 1H, J=1.8, 4.2 Hz, ArH).

35

N-hydroxy-4-(2-(quinolin-8-yl)ethyl)benzamide

36

N-hydroxy-4-((isoquinolin-5-ylamino)methyl)benzamide

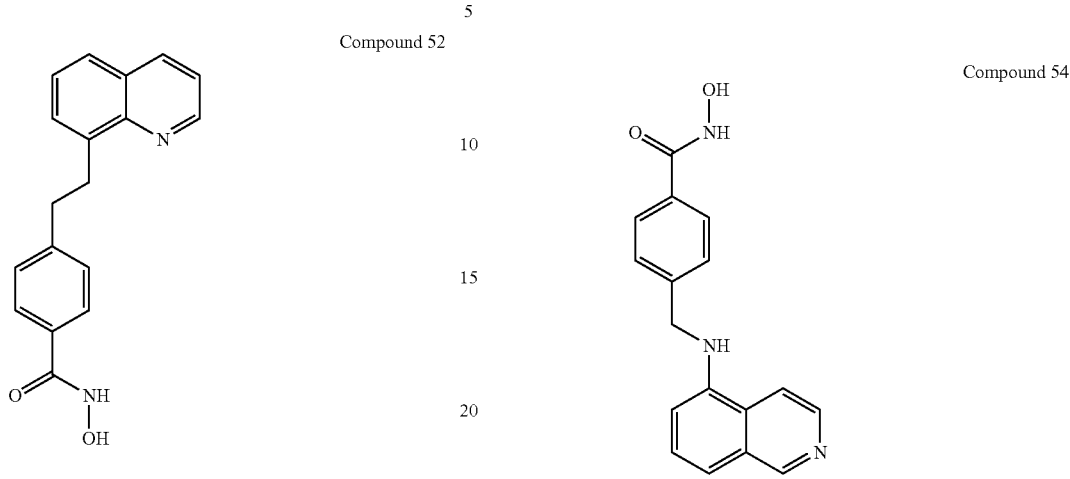

Compound 52

Compound 54

$^1$H NMR (300 MHz, d$_6$-DMSO): δ 3.03-3.09 (m, 2H, CH$_2$), 3.47-3.53 (m, 2H, CH$_2$), 7.30 (d, 1H, J=8.4 Hz, ArH), 7.45-7.58 (m, 3H, ArH), 7.68 (d, 2H, J=8.1 Hz, ArH), 7.81 (dd, 1H, J=1.5, 8.1 Hz, ArH), 8.31-8.35 (m, 1H, ArH), 8.95 (dd, 1H, J=1.8, 4.2 Hz, ArH), 8.98 (s, 1H, NH), 11.15 (s, 1H, OH). HRMS-ESI calcd. for C$_{18}$H$_{16}$N$_2$O$_2$ [M+H]$^+$ 293.1290, found 293.1262.

$^1$H NMR (300 MHz, d$_6$-DMSO): δ 4.55 (d, 2H, J=6.0 Hz, CH$_2$), 6.51 (d, 1H, J=7.5 Hz, ArH), 7.20-7.24 (m, 2H, ArH, NH), 7.31 (t, 1H, J=7.8 Hz, ArH), 7.44 (d, 1H, J=8.1 Hz, ArH), 7.68 (d, 1H, J=8.1 Hz, ArH), 8.11 (d, 1H, J=6.0 Hz, ArH), 8.43 (d, 1H, J=5.7 Hz, ArH), 8.97 (s, 1H, NH), 9.11 (s, 1H, ArH), 11.11 (s, 1H, OH). HRMS-ESI calcd. for C$_{17}$H$_{15}$N$_3$O$_2$ [M+H]$^+$ 294.1243, found 294.1210.

Example 25

Methyl 4-((isoquinolin-5-ylamino)methyl)benzoate

Example 26

Methyl 4-((isoquinolin-8-ylamino)methyl)benzoate

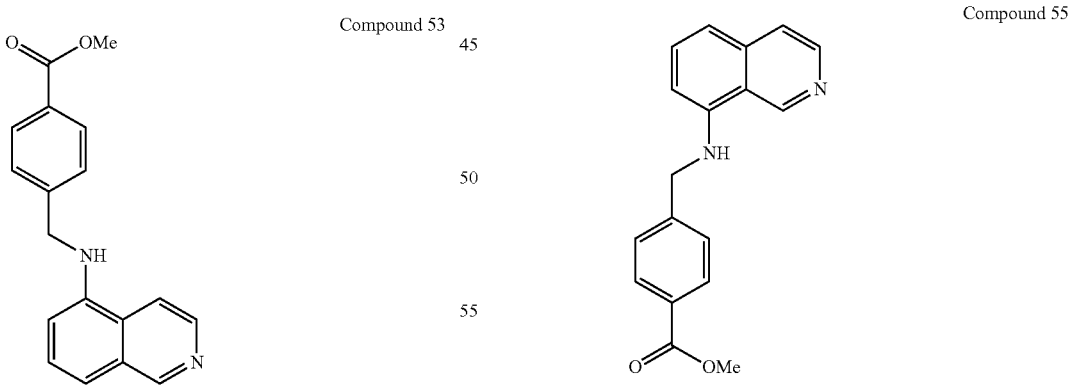

Compound 53

Compound 55

$^1$H NMR (300 MHz, d$_6$-DMSO): δ 3.81 (s, 3H, OCH$_3$), 4.59 (d, 2H, J=5.7 Hz, CH$_2$), 6.48-6.51 (m, 1H, ArH), 7.21-7.34 (m, 3H, ArH, NH), 7.52 (d, 2H, J=8.1 Hz, ArH), 7.90 (d, 2H, J=8.4 Hz, ArH), 8.12 (d, 1H, J=6.0 Hz, ArH), 8.44 (d, 1H, J=6.0 Hz, ArH), 9.12 (s, 1H, ArH).

$^1$H NMR (300 MHz, d$_6$-DMSO): δ 3.35 (s, OCH$_3$), 4.60 (d, 2H, J=5.7 Hz, CH$_2$), 6.39 (d, 1H, J=7.8 Hz, ArH), 7.28 (d, 1H, J=8.1 Hz, ArH), 7.36 (t, 1H, J=7.8 Hz, ArH), 7.54 (d, 2H, J=8.1 Hz, ArH), 7.58-7.66 (m, 1H, ArH, NH), 7.89-7.92 (m, 2H, ArH), 8.40 (d, 1H, J=5.7 Hz, ArH), 9.64 (s, 1H, ArH).

37

N-hydroxy-4-((isoquinolin-8-ylamino)methyl)benz-
amide

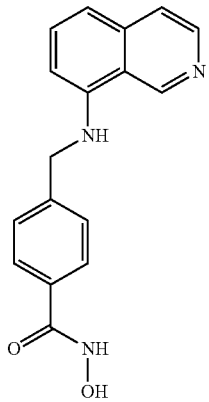

Compound 56

¹H NMR (300 MHz, d₆-DMSO): δ 4.56 (d, 2H, J=5.7 Hz, CH₂), 6.42 (d, 1H, J=7.8 Hz, ArH), 7.02 (d, 1H, J=8.1 Hz, ArH), 7.34-7.40 (m, 1H, ArH), 7.47 (d, 2H, J=8.1 Hz, ArH), 7.58-7.63 (m, 2H, NH, ArH), 7.70 (d, 2H, J=8.1 Hz, ArH), 8.40 (d, 1H, J=5.7 Hz, ArH), 9.03 (brs, 1H, NH), 9.64 (s, 1H, ArH), 11.14 (brs, 1H, OH). HRMS-ESI calcd. for C₁₇H₁₅N₃O₂ [M+H]⁺ 294.1243, found 294.1221.

Example 27

Methyl 4-(quinolin-8-ylamino)benzoate

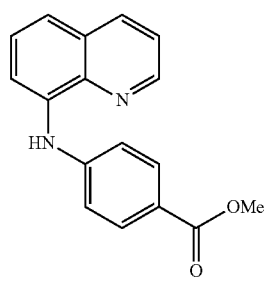

Compound 57

¹H NMR (300 MHz, d₆-DMSO): δ 3.79 (s, 3H, OCH₃), 7.44-7.54 (m, 4H, ArH), 7.56-7.61 (m, 1H, ArH), 7.66-7.70 (m, 1H, ArH), 7.87 (d, 2H, J=9.0 Hz, ArH), 8.32-8.36 (m, 1H, ArH), 8.86-8.89 (m, 1H, ArH), 9.12 (s, 1H, NH).

38

4-(quinolin-8-ylamino)benzoic acid

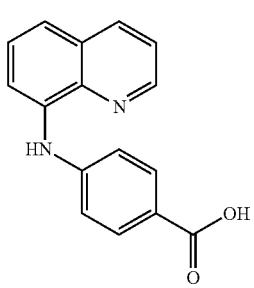

Compound 58

¹H NMR (300 MHz, d₆-DMSO): δ 7.43-7.55 (m, 4H, ArH), 7.60 (dd, 1H, J=1.2, 8.1 Hz, ArH), 7.68 (dd, 1H, J=2.1, 6.9 Hz, ArH), 7.84-7.89 (m, 2H, ArH), 8.35 (dd, 1H, J=1.5, 8.4 Hz, ArH), 8.89 (dd, 1H, J=1.5, 4.2 Hz, ArH), 9.07 (s, 1H, NH), 12.45 (s, 1H, COOH).

N-hydroxy-4-(quinolin-8-ylamino)benzamide

Compound 59

¹H NMR (300 MHz, d₆-DMSO): δ 7.33-7.38 (m, 2H, ArH), 7.57-7.63 (m, 2H, ArH), 7.70-7.78 (m, 4H, ArH), 8.62 (dd, 1H, J=1.5, 8.4 Hz, ArH), 8.97 (dd, 1H, J=1.5, 4.5 Hz, ArH). HRMS-ESI calcd. for C₁₆H₁₃N₃O₂ [M+H]⁺ 280.1086, found 280.1081.

Example 28

Methyl 4-((isoquinolin-1-ylamino)methyl)benzoate

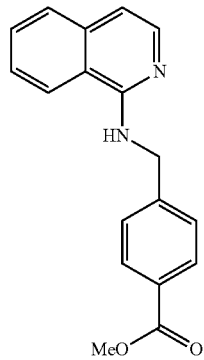

Compound 60

¹H NMR (300 MHz, d₆-DMSO): δ 3.81 (s, 3H, OCH$_3$), 4.81 (d, 2H, J=5.7 Hz, CH$_2$), 6.90 (d, 1H, J=5.7 Hz, ArH), 7.45-7.54 (m, 3H, ArH), 7.60-7.66 (m, 1H, ArH), 7.71 (d, 1H, J=8.1 Hz, ArH), 7.90 (d, 1H, J=5.7 Hz, ArH), 8.88 (d, 2H, J=8.1 Hz, ArH), 8.08 (d, 1H, J=6.0 Hz, NH), 8.30 (d, 1H, J=8.1 Hz, ArH).

N-hydroxy-4-((isoquinolin-1-ylamino)methyl)benzamide

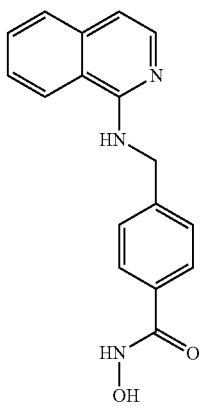

Compound 61

¹H NMR (300 MHz, d₆-DMSO): δ 4.77 (d, 2H, J=5.7 Hz, CH$_2$), 6.89 (d, 1H, J=5.7 Hz, ArH), 7.40 (d, 2H, J=8.1 Hz, ArH), 7.48-7.54 (m, 1H, ArH), 7.59-7.72 (m, 4H, ArH), 7.80 (d, 1H, J=5.7 Hz, ArH), 8.04 (t, 1H, J=6.0 Hz, NH), 8.30 (d, 1H, J=8.1 Hz, ArH), 9.00 (s, 1H, NH), 11.12 (s, 1H, OH). HRMS-ESI calcd. for C$_{17}$H$_{15}$N$_3$O$_2$ [M+H]$^+$ 294.1243, found 294.1208.

Example 29

Methyl 4-((isoquinolin-4-ylamino)methyl)benzoate

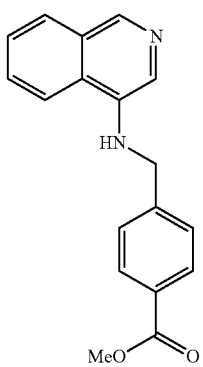

Compound 62

¹H NMR (300 MHz, d₆-DMSO): δ 3.81 (s, 3H, OCH$_3$), 4.62 (d, 2H, J=6.0 Hz, CH$_2$), 7.13 (t, 1H, J=6.0 Hz, NH), 7.52-7.57 (m, 3H, ArH), 7.58-7.64 (m, 1H, ArH), 7.68-7.74 (m, 1H, ArH), 7.90-7.96 (m, 3H, ArH), 8.29 (d, 1H, J=8.4 Hz, ArH), 8.51 (s, 1H, ArH).

N-hydroxy-4-((isoquinolin-4-ylamino)methyl)benzamide

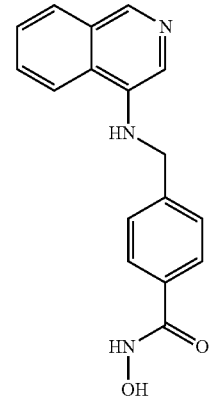

Compound 63

¹H NMR (300 MHz, d₆-DMSO): δ 4.58 (d, 2H, J=6.0 Hz, CH$_2$), 7.13 (d, 1H, J=6.0 Hz, ArH), 7.46-7.54 (m, 3H, ArH), 7.59-7.65 (m, 1H, ArH), 7.67-7.74 (m, 3H, ArH), 7.88-7.96 (m, 1H, ArH), 8.29 (d, 1H, J=8.4 Hz, ArH), 8.98 (s, 1H, NH), 11.13 (s, 1H, OH). HRMS-ESI calcd. for C$_{17}$H$_{15}$N$_3$O$_2$ [M+H]$^+$ 294.1243, found 294.1212.

Example 30

5-Chloroquinoxaline

Compound 64

¹H NMR (300 MHz, d₆-DMSO): δ 7.81-7.88 (m, 1H, ArH), 8.03-8.11 (m, 2H, ArH), 9.04-9.07 (m, 2H, ArH).

Methyl 4-((quinoxalin-5-ylamino)methyl)benzoate

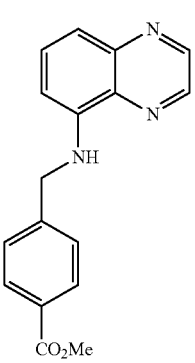

Compound 65

¹H NMR (300 MHz, d₆-DMSO): δ 3.81 (s, 3H, OCH$_3$), 4.63 (d, 2H, J=6.6 Hz, CH$_2$), 6.53 (dd, 1H, J=0.9, 7.8 Hz,

ArH), 7.16 (dd, 1H, J=1.2, 8.4 Hz, ArH), 7.45-7.54 (m, 4H, NH, ArH), 7.87-7.91 (m, 2H, ArH), 8.77 (d, 1H, J=1.8 Hz, ArH), 8.90 (d, 1H, J=1.8 Hz, ArH).

N-hydroxy-4-((quinoxalin-5-ylamino)methyl)benzamide

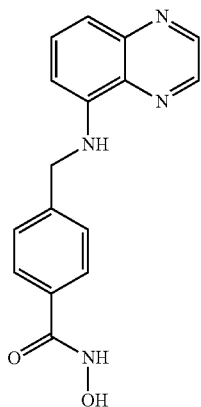

Compound 66

$^1$H NMR (300 MHz, d$_6$-DMSO): δ 4.59 (d, 2H, J=6.6 Hz, CH$_2$), 6.56 (dd, 1H, J=0.6, 7.8 Hz, ArH), 7.16 (dd, 1H, J=0.9, 8.4 Hz, ArH), 7.43-7.52 (m, 4H, NH, ArH), 7.68 (d, 2H, J=8.4 Hz, ArH), 8.77 (d, 1H, J=1.8 Hz, ArH), 8.89 (d, 1H, J=1.8 Hz, ArH), 8.97 (brs, 1H, NH), 11.12 (brs, 1H, OH). HRMS-ESI calcd. for C$_{16}$H$_{14}$N$_4$O$_2$ [M+H]$^+$ 295.1195, found 295.1190.

Example 31

Methyl 4-(((2-methylquinolin-8-yl)amino)methyl)benzoate

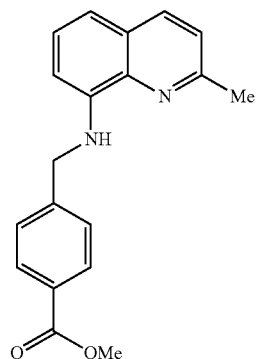

Compound 67

The solid compound was obtained from 6a (0.6 g, 3.72 mmol) according to method A of general procedure A (0.9 g, 79%). $^1$H NMR (300 MHz, CDCl$_3$): δ 2.71 (s, 3H, CH$_3$), 3.91 (s, 3H, OCH$_3$), 6.36 (d, 2H, J=6.0 Hz, CH$_2$), 6.52 (dd, 1H, J=0.6, 7.5 Hz), 6.72-6.77 (m, 1H, NH), 7.01-7.05 (m, 1H, ArH), 7.20-7.28 (m, 2H, ArH), 7.50 (d, 1H, J=8.4 Hz, ArH), 7.94-8.03 (m, 3H, ArH)

N-hydroxy-4-(((2-methylquinolin-8-yl)amino)methyl)benzamide

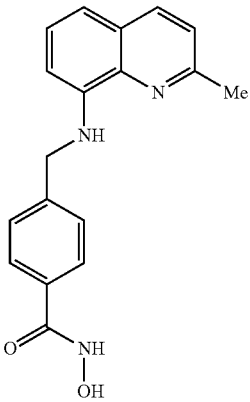

Compound 68

The solid compound was obtained from 67 (0.83 g, 2.71 mmol) according to general procedure C (0.76 g, 91%). $^1$H NMR (300 MHz, DMSO-d$_6$): δ 2.67 (s, 3H, CH$_3$), 4.57 (d, 2H, J=6.6 Hz, CH$_2$), 6.47 (d, 1H, J=7.5 Hz, ArH), 6.97-7.05 (m, 2H, NH, ArH), 7.17 (t, 1H, J=8.1 Hz, ArH), 7.38 (d, 1H, J=8.1 Hz, ArH), 7.44 (d, 2H, J=7.8 Hz, ArH), 7.68 (d, 2H, J=8.1 Hz, ArH), 8.08 (d, 1H, J=8.4 Hz, ArH), 8.96 (brs, 1H, NH), 11.11 (brs, 1H, OH). HRMS-ESI Calcd. for C$_{18}$H$_{17}$N$_3$O$_2$ [M+H]$^+$ 308.1448, found 308.1399.

Example 32

Methyl 4-((quinolin-8-yloxy)methyl)benzoate

Compound 70

A solution of 6b (0.6 g, 4.2 mmol), methyl 4-(chloromethyl)benzoate (0.87 g, 4.62 mmol) and potassium carbonatein (1.16 g, 8.4 mmol) in acetone (10 mL) was heated to reflux for 12 h. Subsequently, the mixture was filtered. The organic layer was collected and purified through chromatography (ethyl acetare/hexane) to provide the product (1.1 g, 89%). $^1$H NMR (300 MHz, DMSO-d$_6$): δ 3.85 (s, 3H, OCH$_3$), 5.42 (s, 2H, CH$_2$), 7.25-7.29 (m, 1H, ArH), 7.46-7.59 (m, 3H, ArH), 7.69 (d, 2H, J=8.1 Hz, ArH), 7.99-8.03 (m, 2H, ArH), 8.30-8.34 (m, 1H, ArH), 8.86-8.89 (m, 1H, ArH).

N-hydroxy-4-((quinolin-8-yloxy)methyl)benzamide

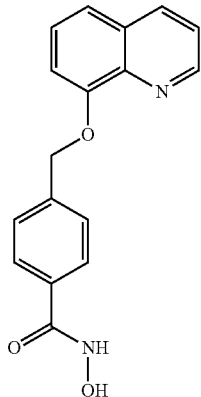

Compound 71

The solid compound was obtained from 70 (0.6 g, 2.05 mmol) according to general procedure C (0.54 g, 90%). $^1$H NMR (300 MHz, DMSO-d$_6$): δ 5.37 (s, 2H, CH$_2$), 7.25-7.29 (m, 1H, ArH), 7.46-7.57 (m, 3H, ArH), 7.61 (d, 2H, J=8.1 Hz, ArH), 7.78 (d, 2H, J=8.1 Hz, ArH), 8.30-8.34 (m, 1H, ArH), 8.85-8.88 (m, 1H, ArH), 9.03 (brs, 1H, NH), 11.22 (brs, 1H, OH). HRMS-ESI Calcd. for C$_{17}$H$_{14}$N$_2$O$_3$ [M+H]$^+$ 295.1083, found 295.1057.

Example 33

Methyl 4-((quinolin-8-ylthio)methyl)benzoate

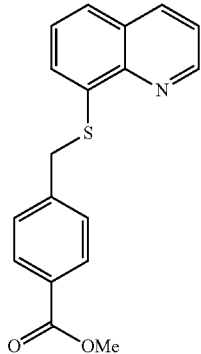

Compound 72

A solution of 8-mercaptoquinoline hydrochloride (6c) (0.36 g, 1.74 mmol), methyl 4-(chloromethyl)benzoate (0.36 g, 1.92 mmol), triethylamine (0.3 mL, 2.09 mmol) and potassium carbonatein (0.49 g, 3.48 mmol) in acetone (10 mL) was heated to reflux for 12 h. Subsequently, the mixture was filtered. The organic layer was collected and purified through chromatography (ethyl acetare/hexane) to provide the product (0.48 g, 89%). $^1$H NMR (300 MHz, DMSO-d$_6$): δ 3.82 (s, 3H, OCH$_3$), 4.43 (s, 2H, CH$_2$), 7.46-7.52 (m, 1H, ArH), 7.55-7.64 (m, 4H, ArH), 7.69-7.73 (m, 1H, ArH), 7.89-7.92 (m, 2H, ArH), 8.35 (dd, 1H, J=1.8, 8.4 Hz, ArH), 8.88 (dd, 1H, J=1.8, 4.2 Hz, ArH).

N-hydroxy-4-((quinolin-8-ylthio)methyl)benzamide

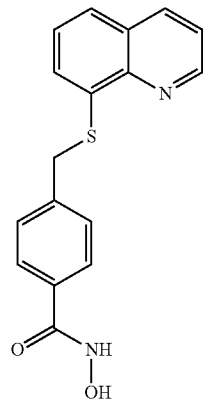

Compound 73

The solid compound was obtained from 72 (0.6 g, 1.86 mmol) according to general procedure C (0.53 g, 92%). $^1$H NMR (300 MHz, DMSO-d$_6$): δ 4.38 (s, 2H, CH$_2$), 7.47-7.61 (m, 5H, ArH), 7.68-7.73 (m, 3H, ArH), 8.35 (dd, 1H, J=1.2, 8.4 Hz, ArH), 8.88 (dd, 1H, J=1.8, 4.2 Hz, ArH), 9.00 (brs, 1H, NH), 11.17 (brs, 1H, OH). HRMS-ESI Calcd. for C$_{17}$H$_{14}$N$_2$O$_2$S [M+H]$^+$311.0854, found 311.0848.

Example 34

Methyl 4-(quinolin-8-ylmethylamino)benzoate

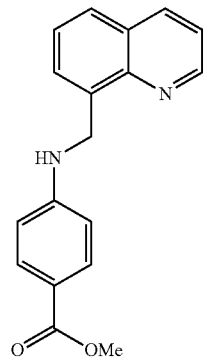

Compound 76

The solid compound was obtained from 6d (0.67 g, 4.28 mmol) and methyl 4-aminobenzoate (0.6 g, 3.89 mmol) according to method A of general procedure A (1.03 g, 82%). $^1$H NMR (300 MHz, DMSO-d$_6$): δ 3.71 (s, 3H, OCH$_3$), 4.98 (s, 2H, CH$_2$), 6.61-6.65 (m, 2H, ArH), 7.14-7.18 (m, 1H, NH), 7.25-7.67 (m, 5H, ArH), 7.88 (d, 1H, J=8.1 Hz, ArH), 8.37-8.41 (m, 1H, ArH), 8.97-8.99 (m, 1H, ArH).

N-hydroxy-4-(quinolin-8-ylmethylamino)benzamide

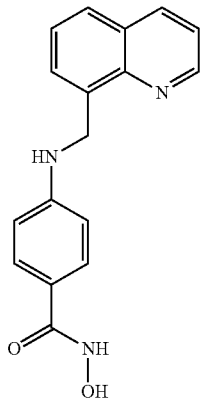

Compound 75

The solid compound was obtained from 76 (0.6 g, 2.05 mmol) according to general procedure C (0.52 g, 87%). $^1$H NMR (300 MHz, DMSO-$d_6$): δ 4.95 (d, 2H, J=6.0 Hz, CH$_2$), 6.57 (d, 2H, J=8.7 Hz, ArH), 6.79-6.84 (m, 1H, NH), 7.45-7.68 (m, 5H, NH), 7.87 (d, 1H, J=8.1 Hz, ArH), 8.37-8.41 (m, 1H, ArH), 8.64 (s, 1H, NH), 8.96-8.99 (m, 1H, ArH), 10.71 (brs, 1H, OH). HRMS-ESI Calcd. for $C_{17}H_{15}N_3O_2$ [M+H]$^+$ 294.1243, found 294.1238.

Example 35

N-Hydroxy-4-(quinolin-8-ylaminomethyl)-benzamide mesylate

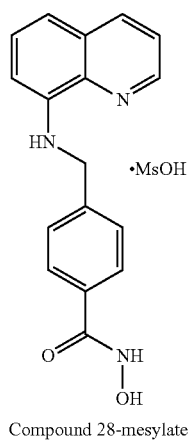 [SMILES: "·MsOH" ; O=C(NO)c1ccc(CNc2cccc3cccnc23)cc1]

Compound 28-mesylate

To a solution of Compound 28 in dioxane (0.2 M) was added a solution of MsOH in dioxane (0.2 M) and the resulting mixture was allowed to stir at room temperature. The reaction mixture was filtered and washed with dioxane to afford Compound 28-mesylate. $^1$H-NMR (300 MHz, DMSO-$d_6$) δ 2.34 (s, 3H), 4.59 (s, 2H), 6.56 (dd, J=0.9, 7.8 Hz, 1H), 7.08 (dd, J=1.2, 8.1 Hz, 1H), 7.26-7.32 (m, 1H), 7.46 (d, J=8.4 Hz, 2H), 7.55 (dd, J=8.4, 8.4 Hz, 1H), 7.68 (d, J=8.1 Hz, 2H), 8.26 (dd, J=1.8, 8.4 Hz, 1H); Anal. Calcd for $C_{18}H_{19}N_3O_5S$: C, 55.52; H, 4.92; N, 10.79; S, 8.23. Found: C, 55.65; H, 4.81; N, 10.72; S, 7.91; HPLC purity of 98.83% (retention time=26.42).

Example 36

A study was conducted to evaluate the inhibitory activity of compounds of Formula (I) in inhibiting HDAC6, antiproliferative activity of test compounds in suppressing cancer cell growth, and selectivity of inhibiting HDAC6 over other HDAC isoforms.

Fluorogenic HDAC assay kits were used to assess the ability of HDAC inhibitors to inhibit deacetylation of lysine residues on a substrate by recombinant proteins HDAC1, 3, 4, 5, 6, 7, 8, 9 and Sirt1 according to the manufacturer's instructions (BPS Bioscience Corp., San Diego, Calif., USA).

The study was performed according to the protocol reported in Hsieh et al., *Cell Death and Disease*, 2014, April; 5:e1166.

It was observed that multiple compounds unexpectedly exhibited significant HDAC6 inhibitory activity (measured by their half maximal inhibitory concentration or IC$_{50}$), as shown in Table 1 below. More specifically, 9 compounds demonstrated remarkable HDAC6 inhibition with IC$_{50}$ values of <25 nM. In particular, Compounds 12 and 28 demonstrated extraordinary HDAC6 inhibition with IC$_{50}$ values of 2.73 and 4.41 nM, respectively.

As also shown in Table 1, eight of the nine compounds demonstrated HDAC1 inhibition with IC$_{50}$ values of 0.78-6.70 μM.

TABLE 1

HDAC1/6 enzyme inhibitory activities of test compounds

| | Enzyme IC$_{50}$ | |
|---|---|---|
| Compound | HDAC1 (μM) | HDAC6 (nM) |
| 4 | 0.78 | 19.11 |
| 20 | >100 | 18.98 |
| 12 | 2.65 | 2.73 |
| 68 | 1.69 | 12.07 |
| 28 | 6.70 | 4.41 |
| 71 | 2.56 | 11.04 |
| 73 | 2.2 | 23.38 |
| 75 | 2.04 | 10.98 |
| 12 | | 2.73 |
| Tubastatin A | 9.5 | 26.16 |

Shown in Table 2 below are antiproliferative activities (measured by their half maximal concentration for inhibiting cell growth, i.e., GI$_{50}$) of the test compounds against various cancer cell lines.

Unexpectedly, a number of compounds of formula (I) demonstrated high potency with GI50<10 μM in six cancer cell lines, i.e., PC-3, A549, HCT116, HL60, MDA-MB-231, and T98 cell lines.

TABLE 2

Antiproliferative activities of test compounds

| Compound | Cancer cell lines (GI$_{50}$ μM) | | | | | |
|---|---|---|---|---|---|---|
| | PC-3 prostate | A549 lung | HCT116 colorectal | HL60 leukemia | MDA-MB-231 Breast | T98 Glioblastoma |
| 4 | 1.62 ± 0.20 | 2.73 ± 0.24 | | | | |
| 20 | >10 | >10 | | | | |
| 12 | 3.28 ± 0.11 | 5.53 ± 0.24 | | | | |
| 68 | 4.45 ± 0.92 | 5.89 ± 0.42 | | | | |
| 28 | 3.40 ± 0.13 | 5.24 ± 0.18 | | | 1.89 ± 0.33 | 9.89 ± 0.92 |
| 28-mesylate | | | | | 1.36 ± 0.25 | 10.75 ± 0.83 |
| 71 | 6.23 ± 0.32 | 7.81 ± 1.17 | | | | |
| 73 | 4.29 ± 0.70 | 6.11 ± 0.69 | | | | |
| 75 | >10 | 6.32 ± 0.92 | | | | |
| 12 | 3.28 ± 0.11 | 5.53 ± 0.24 | | | | |
| 40 | 0.85 ± 0.09 | | 0.29 ± 0.02 | | | |
| 42 | 2.64 ± 0.14 | | 0.62 ± 0.03 | | | |
| 44 | | | 3.28 ± 0.48 | | | |
| 54 | 6.06 ± 0.40 | 4.64 ± 0.25 | | | | |
| 56 | 4.91 ± 0.24 | 1.76 ± 0.21 | | | | |
| 61 | | | 0.66 ± 0.10 | 1.17 ± 0.23 | | |
| 63 | | | 1.20 ± 0.14 | 1.96 ± 0.16 | | |
| 66 | | | 1.95 ± 0.21 | 5.58 ± 0.15 | | |
| 59 | | | 3.32 ± 0.21 | 6.64 ± 0.69 | | |
| 52 | 9.66 ± 0.07 | | 3.05 ± 0.09 | | | |
| 6 | 0.38 ± 0.03 | 0.71 ± 0.01 | | | | |
| 8 | >10 | >10 | | | | |
| 10 | >10 | >10 | | | | |
| 22 | >10 | >10 | | | | |
| 26 | >10 | >10 | | | | |
| 24 | >10 | >10 | | | | |
| 14 | 0.62 ± 0.05 | 1.25 ± 0.08 | | | | |
| 16 | >10 | >10 | | | | |
| 18 | >10 | >10 | | | | |
| 30 | 1.25 ± 0.02 | 1.11 ± 0.05 | | | | |
| 32 | >10 | >10 | | | | |
| 34 | 3.51 ± 0.18 | 4.26 ± 0.07 | | | | |
| 47 | 2.08 ± 0.10 | 7.77 ± 0.03 | | | | |
| 50 | >10 | >10 | | | | |
| 36 | >10 | | >10 | | | |
| 38 | >10 | | >10 | | | |
| Tubastatin A | 48.19 ± 0.43 | 52.2 ± 1.28 | | | | |

Table 3 below indicated selectivity of compounds inhibiting HDAC6 over other HDACs including HDAC1, 3, 4, 5, 7, 8, 9 and Sirt1.

Unexpectedly, both Compounds 12 and 28 demonstrated selectivity of >100 folds over all the other tested HDACs. Most unexpectedly, Compound 12 exhibited remarkable selectivity of >1000 folds over all the other HDACs.

TABLE 3

Selectivity over other HDAC isoforms

| Compound | Selectivity (fold) | | | | | | | |
|---|---|---|---|---|---|---|---|---|
| | HDAC6 v.s. HDAC1 | HDAC6 v.s. HDAC3 | HDAC6 v.s. HDAC4 | HDAC6 v.s. HDAC5 | HDAC6 v.s. HDAC7 | HDAC6 v.s. HDAC8 | HDAC6 v.s. HDAC9 | HDAC6 v.s. Sirt1 |
| 28 | 181.27 | 442.46 | >1000 | 980.91 | 830.70 | 327.74 | >1000 | >10000 |
| 12 | >1000 | >1000 | >1000 | >1000 | >1000 | >2000 | >5000 | >10000 |
| Tubastatin A | 517.57 | 487.39 | 625.02 | 163.24 | 761.89 | 167.76 | >1000 | 15.34 |

Example 37

A study was conducted to evaluate the activity of a compound of Formula (I) in increasing acetyl-a-tubuline expression in human multiple myeloma cell lines (RPMI8226, U266, and NCI-H929).

Cells (1×10$^6$) were incubated for 10 minutes at 4° C. in a lysis buffer solution in a culture vessel, and then scraped off the culture vessel, incubated on ice for another 10 minutes, and centrifuged at 17,000×g for 30 minutes at 4° C. Protein samples (80 μg) were electrophoresed on SDS gels and transferred onto a nitrocellulose membrane, which was blocked by incubation with 5% fat-free milk in phosphate-buffered saline (PBS) for 30 minutes at room temperature. Immunoblotting was performed by overnight incubation at 4° C. with primary antibodies in PBS, followed by incubation for 1 hour at room temperature with horseradish peroxidase (HRP)-conjugated secondary antibodies, then bound antibodies were measured using enhanced chemiluminescence (ECL) reagent (Advansta Corp., Menlo Park, Calif., USA) and exposure to photographic film.

The study was performed according to the protocol reported in Yang et al., *Journal of Molecular Medicine*, 2014, November; 92(11):1147-1158.

Compound 28 unexpectedly exerted activity in increasing acetyl-a-tubuline expression in a dose-dependent manner in all three human multiple myeloma cell lines, i.e., RPMI8226, U266, and NCI-H929.

Example 38

A study was conducted to evaluate the activity of a compound of Formula (I) in inhibiting HDAC6-dynein binding and inducing accumulation of polyubiquited proteins.

Cell lysates were immunoprecipitated overnight at 4° C. with 1 µg of dynein antibody and A/G-agarose beads. The precipitated beads were washed three times with 1 mL of an ice-cold cell lysis buffer solution. The resulting immune complex was resolved by 10% SDS-PAGE gel electrophoresis, followed by immunoblotting assay using anti-HDAC6 Ab.

The study was performed according to the protocol reported in Chen et al., *Journal of Immunology*, 2008, 181(12):8441-8449.

It was observed that Compound 28 unexpectedly inhibited HDAC6-dynein binding and induced accumulation of polyubiquited proteins both in a dose-dependent manner.

Example 39

A study was conducted to evaluate the effect of a compound of Formula (I) combined with bortezomib in inducing apoptosis in multiple myeloma cells.

To detect cell cycle progression, cells were incubated with or without the indicated agent for 24 hours, washed twice with ice-cold PBS, collected by centrifugation, and fixed in 70% (v/v) ethanol for 2 hours at −20° C. They were subsequently incubated for 30 minutes at room temperature with 0.2 mL of deoxyribonucleic acid (DNA) extraction buffer (0.2 M $Na_2HPO_4$ and 0.1 M citric acid buffer, pH 7.8), re-suspended in 1 mL of propidium iodide staining buffer (0.1% Triton X-100, 100 µg/mL of RNase A, and 80 µg/mL of propidium iodide in PBS), incubated at 37° C. for 30 minutes in darkness, sorted by FACScan, and analyzed using CellQuest software (BD Biosciences).

The study was performed according to the protocol reported in Hsieh et al., *Cell Death and Disease*, 2014, April; 5:e1166.

Unexpectedly, Compound 28 combined with bortezomib synergistically induced apoptosis in all three human multiple myeloma cell lines, i.e., RPMI8226, U266, and NCI-H929.

Example 40

A study was conducted to evaluate the effect of a compound of Formula (I) combined with bortezomib in increasing cleavage of Caspase-3, Caspase-8, and Caspase-9 in multiple myeloma cells.

Cells ($1\times10^6$) were incubated for 10 minutes at 4° C. in a lysis buffer solution in a culture vessel, and then scraped off the culture vessel, incubated on ice for another 10 minutes, and centrifuged at 17,000×g for 30 minutes at 4° C. Protein samples (80 µs) were electrophoresed on SDS gels and transferred onto a nitrocellulose membrane, which was blocked by incubation with 5% fat-free milk in phosphate-buffered saline (PBS) for 30 minutes at room temperature. Immunoblotting was performed by overnight incubation at 4° C. with primary antibodies in PBS, followed by incubation for 1 hour at room temperature with horseradish peroxidase (HRP)-conjugated secondary antibodies, then bound antibodies were measured using enhanced chemiluminescence (ECL) reagent (Advansta Corp., Menlo Park, Calif., USA) and exposure to photographic film.

The study was performed according to the protocol reported in Yang et al., *Journal of Molecular Medicine*, 2014, November; 92(11):1147-1158.

Compound 28 combined with bortezomib unexpectedly increased cleavage of Caspase-3, Caspase-8, and Caspase-9 in multiple myeloma cells of RPMI8226 and NCI-H929.

Example 41

A study was conducted to evaluate the effect of compounds of Formula (I) in amyloid precursor protein (APP) levels and $A\beta_{42}$ production.

Neuro 2a cells ($1\times10^6$) in 6-well plates were transfected with pCAX APP 695 plasmid for 24 hours, then incubated for another 24 hours with Compound 12, Compound 28, or tubasatin A (0.1-10 µM). Cells were then harvested and cell lysates were prepared for Western blot analysis of the APP proteins.

Moreover, neuro 2a or SH—SYSY cells ($1\times10^5$) were transfected with pCAX APP 695 plasmid for 24 hours, followed by incubation with Compound 12 or Compound 28 (0.1-10 µM) for another 24 hours. Cell culture supernatants were assayed for $A\beta_{42}$ production.

As a control experiment, neuro 2a cells transfected with pCAX APP 695 plasmid significantly increased APP levels. Unexpectedly, Compounds 12 and 28 markedly reduced the APP expression. In addition, these two compounds also decreased $A\beta_{42}$ production in pCAX APP 695 plasmid-transfected Neuro 2a and SH—SYSY cells.

Example 42

An in vivo study was conducted to evaluate the efficacy of compounds of Formula (I) in suppressing tumor growth in multiple human cancer types.

Eight-week-old athymic nude mice were group-housed under conditions of constant photoperiod (12 h light/12 h dark at 21-23° C. and 60-85% humidity) with ad libitum access to sterilized food and water. All animal experiments followed ethical standards, and protocols were reviewed and approved by the Animal Use and Management Committee of National Taiwan University. Each mouse was inoculated subcutaneously with $1\times10^6$~$1\times10^7$ human cancer cells in a total volume of 0.1 mL serum-free medium containing 50% Matrigel (BD Biosciences). As tumors became established (~100 $mm^3$), mice were randomized to various groups to be treated with pre-determined materials (n=6-8/group): (i) control group: 0.5% DMSO/0.5% Cremophor/90% D5W and (ii) treatment groups: Compounds 12 and 28 at pre-determined doses daily. Mice received treatment by intraperitoneal injection for the duration of the study. Tumors were measured weekly using calipers. Tumor size, in $mm^3$, was calculated according to the formula: Tumor volume=($w^2\times$ l)/2, where w and l respectively represent the width and length (both in mm) of the tumor.

As shown in Table 3 below, both Compounds 12 and 28 unexpectedly demonstrated significant efficacy in inhibiting tumor growth of various human cancers.

TABLE 3

Efficacy of HDAC6 inhibitors in tumor growth inhibition (TGI)

| Tumor Line | Tumor Type | HDAC6 Inhibitor | Dose/Schedule | % TGI | Best Response |
|---|---|---|---|---|---|
| Hematological tumor | | | | | |
| RPMI-8226 | Multiple myeloma | Compound 28 | 50 mg/kg, qd | 80.0% | 2 × CR[a] |
| HL-60 | Acute promyelocytic leukemia | Compound 28 | 25 mg/kg, qd | 47.4% | |
| | | Compound 28 | 50 mg/kg, qd | 61.1% | |
| | | Compound 12 | 50 mg/kg, qd | 72.2% | |
| BJAB | Burkitt lymphoma-derived B-cell | Compound 28 | 25 mg/kg, qd | 40.8% | |
| | | Compound 28 | 50 mg/kg, qd | 74.0% | |
| | | Compound 12 | 50 mg/kg, qd | 64.5% | |
| Solid tumor | | | | | |
| MDA-MB-231 | Breast | Compound 28 | 25 mg/kg, qd | 38.6% | |
| | | Compound 28 | 50 mg/kg, qd | 56.4% | |
| HCT116 | Colorectal | Compound 28 | 50 mg/kg, qd | 9.1% | |
| | | Compound 28 | 100 mg/kg, qd | 44.4% | |

[a]CR: complete regression

No significant body weight change was observed in animals in the above-described study.

In addition, both Compounds 12 and 28 were studied to evaluate their safety in animals.

ICR (Crl:CD1) strain mice were administered each of Compounds 12 and 28 at doses of 50, 100, and 200 mg/kg. The animals were dosed intraperitoneally once a day for 7 days and then monitored for another 7 days. The animals were weighed daily for 1 week and then twice weekly.

It was observed that both Compounds 12 and 28 were well tolerated at all three doses of 50, 100, and 200 mg/kg.

Example 43

An in vivo study was conducted to evaluate the efficacy of compounds of Formula (I) in improving memory deficits associated with Alzheimer's disease.

Compound 12, Compound 28, suberanilohydroxamic acid (50 mg/kg) or vehicle was given to rats by gavage twice daily for seven days prior to behavioral experiments. On the day conducting a behavior assessment, rats in all groups except the control group were administered scopolamine (1.5 mg/kg) by intraperitoneal injection for 30 minutes before the assessment, then a water maze test or an elevated plus maze test was performed.

In the mater maze test, time spent in the correct quadrant was significantly deceased in scopolamine-treated rats compared with that of the control group. Unexpectedly, treatment with each of Compounds 12 and 28 was found to markedly reverse this effect.

Furthermore, scopolamine treatment significantly increased transfer latency time in the elevated plus maze test. Unexpectedly, treatment with each of Compounds 12 and 28 significantly rescued scopolamine-mediated increase of transfer latency time. The significant reduction in transfer latency time indicated improvement in memory.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

Further, from the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

We claim:

1. An HDAC6-selective inhibiting compound of formula (I) or a pharmaceutically acceptable salt thereof:

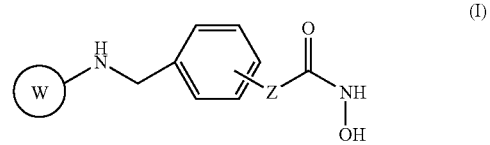

(I)

in which

W is quinoline;

and

Z is a bond, methylene, or —CH═CH—.

2. The compound or pharmaceutically acceptable salt of claim 1, wherein Z is a bond.

3. The compound or pharmaceutically acceptable salt of claim 1, wherein W is

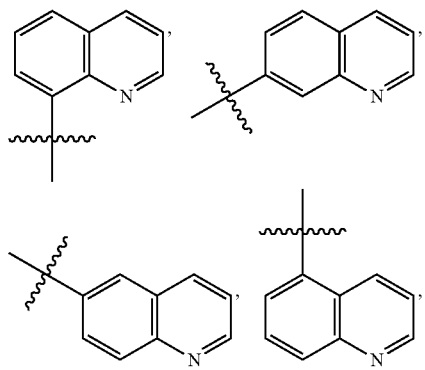

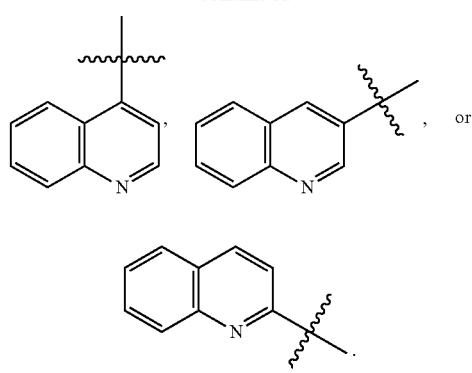
4. The compound or pharmaceutically acceptable salt of claim 1, wherein the phenylene adjacent to Z is para-phenylene or meta-phenylene.
5. A compound or pharmaceutically acceptable salt selected from:
Compound 4
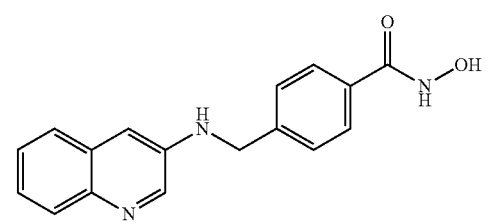
Compound 6
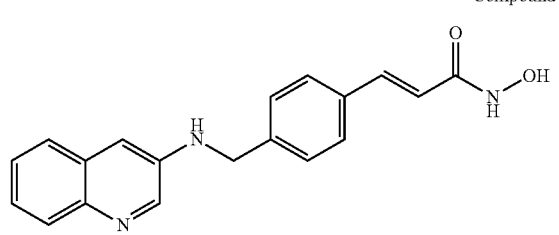
Compound 12
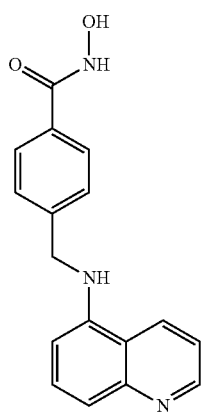
Compound 14
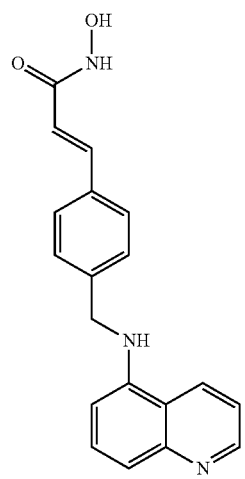
Compound 20
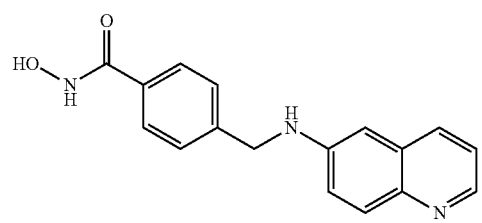
Compound 22
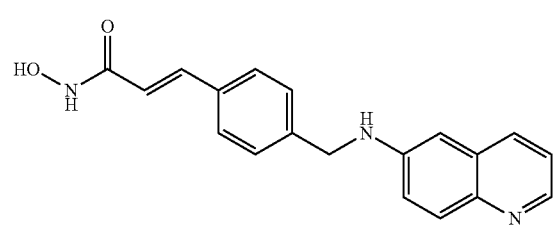
Compound 28
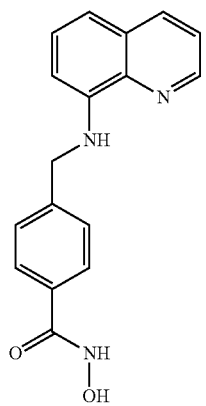

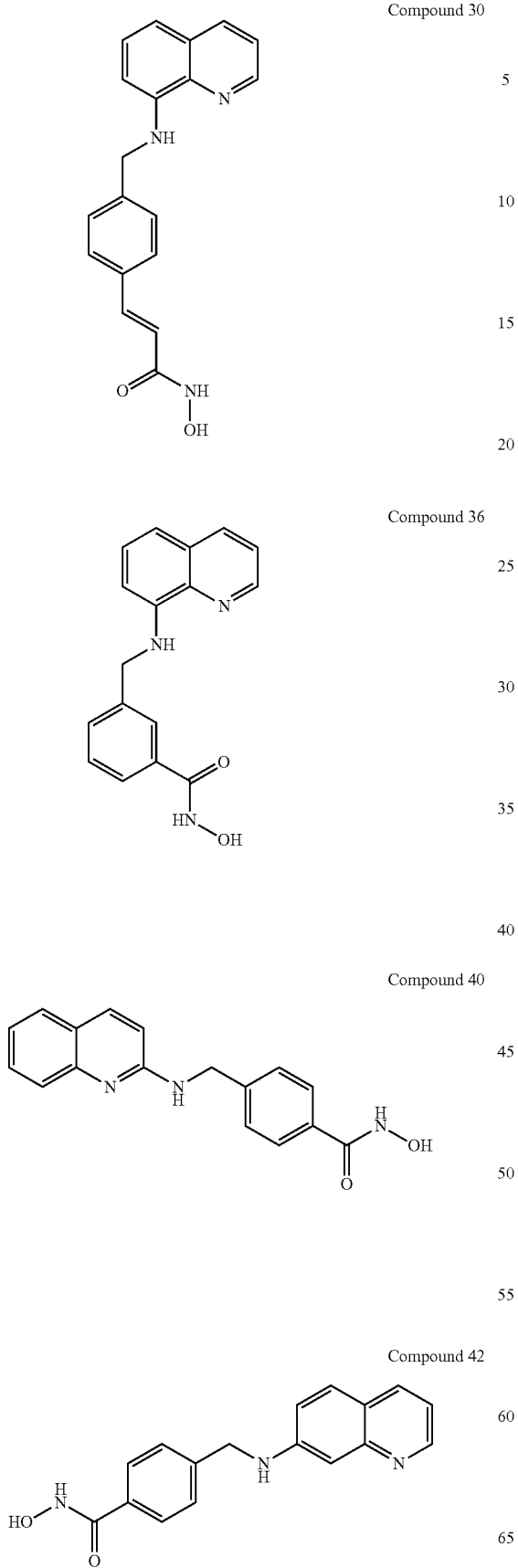

-continued

Compound 63

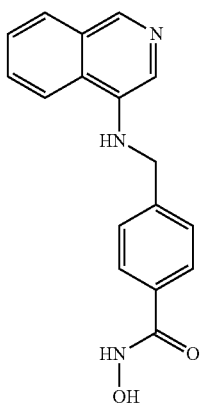

Compound 68

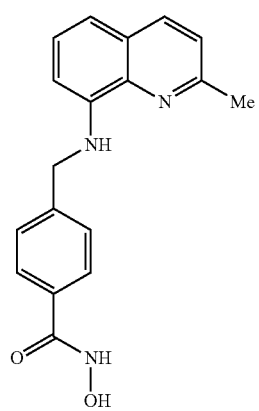

Compound 28-mesylate

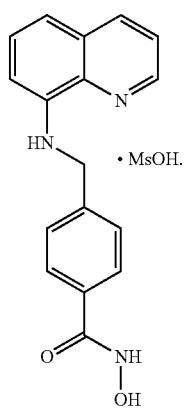

6. A pharmaceutical composition comprising a pharmaceutically acceptable carrier and a compound or pharmaceutically acceptable salt of claim 1.

7. The pharmaceutical composition of claim 6, wherein the compound or pharmaceutically acceptable salt is selected from:

Compound 12

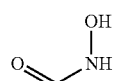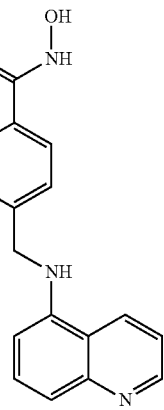

Compound 28

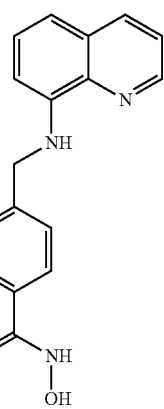

Compound 28-mesylate

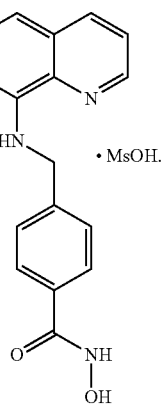

8. An HDAC6-selective inhibiting compound of formula (I) or a pharmaceutically acceptable salt thereof:

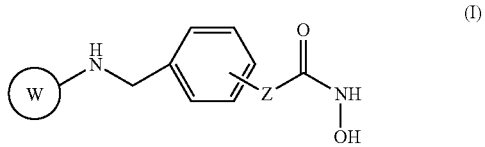

(I)

in which
Z is a bond, methylene, or —CH=CH—; and
W is
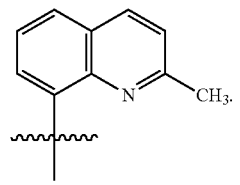 [SMILES: *c1cccc2ccc(C)nc12]
* * * * *